US006768865B2

(12) United States Patent
Stathakis et al.

(10) Patent No.: US 6,768,865 B2
(45) Date of Patent: Jul. 27, 2004

(54) LIQUID VAPORIZATION WITH HOUSING STABILIZATION SYSTEM

(75) Inventors: Kristopher J. Stathakis, Scottsdale, AZ (US); Christopher Wolpert, Scottsdale, AZ (US); Lawrence T. Levine, Easton, CT (US); Carl Triplett, Scottsdale, AZ (US); Mengtao Pete He, Scottsdale, AZ (US); Debra Park, Mesa, AZ (US)

(73) Assignee: The Dial Corporation, Scottsdale, AZ (US)

( * ) Notice: Subject to any disclaimer, the term of this patent is extended or adjusted under 35 U.S.C. 154(b) by 114 days.

(21) Appl. No.: 10/018,705

(22) PCT Filed: Jun. 13, 2001

(86) PCT No.: PCT/US00/16197

§ 371 (c)(1),
(2), (4) Date: May 24, 2002

(87) PCT Pub. No.: WO00/76292

PCT Pub. Date: Dec. 21, 2000

(65) Prior Publication Data

US 2002/0172512 A1 Nov. 21, 2002

(51) Int. Cl.[7] .................................................. F24F 6/00
(52) U.S. Cl. ....................................... 392/395; 392/392
(58) Field of Search ................................. 392/386, 390, 392/391, 392, 394, 395

(56) References Cited

U.S. PATENT DOCUMENTS

| | | |
|---|---|---|
| 1,944,821 A | 1/1934 | Blaise |
| 1,994,932 A | 3/1935 | Vidal |
| D159,407 S | 7/1950 | Costello |
| 2,597,195 A | 5/1952 | Smith et al. |
| 2,611,068 A | 9/1952 | Wellens |
| D189,420 S | 12/1960 | Diehl |
| 3,872,280 A | 3/1975 | Van Dalen |
| 4,467,177 A | 8/1984 | Zobele |
| 4,663,315 A | 5/1987 | Hasegawa et al. |
| 4,731,520 A | 3/1988 | Glucksman et al. |
| 4,739,928 A | 4/1988 | O'Neil |
| 4,745,705 A | 5/1988 | Yamamoto et al. |
| D307,180 S | 4/1990 | Luthy |
| 5,038,394 A | 8/1991 | Hasegawa et al. |
| 5,095,647 A | 3/1992 | Zobele et al. |
| 5,111,477 A | 5/1992 | Muderlak |
| 5,161,646 A | 11/1992 | Aurich et al. |
| D335,530 S | 5/1993 | Schimanski |
| 5,222,186 A | 6/1993 | Schimanski et al. |
| 5,290,546 A | 3/1994 | Hasegawa et al. |
| D346,207 S | 4/1994 | Martin |
| D357,330 S | 4/1995 | Wong et al. |
| 5,484,086 A | 1/1996 | Pu |
| 5,591,395 A | 1/1997 | Schroeder et al. |
| D381,443 S | 7/1997 | Yuen |
| 5,647,053 A | 7/1997 | Schroeder et al. |
| D393,063 S | 3/1998 | Wefler |
| 5,773,795 A | 6/1998 | Messmer |
| D407,476 S | 3/1999 | Goeren et al. |
| 5,909,845 A | 6/1999 | Greatbatch et al. |
| 5,926,614 A | 7/1999 | Steinel |
| 5,940,577 A | 8/1999 | Steinel |
| 6,104,867 A | 8/2000 | Stathakis et al. |

FOREIGN PATENT DOCUMENTS

| | | |
|---|---|---|
| WO | WO 91/15249 | 3/1991 |
| WO | WO 98/19526 | 11/1997 |
| ZA | 968433 | 10/1996 |

Primary Examiner—Sang Y. Paik
(74) Attorney, Agent, or Firm—Snell & Wilmer LLP

(57) ABSTRACT

A liquid vaporizer is provided which includes a housing stabilization system for stabilizing the vaporizer when it is plugged into a wall outlet. In an exemplary embodiment of the invention, the stabilization system comprises one or more projections which abut the wall or outlet to which the vaporizer is inserted. The liquid vaporizer stabilization system may also serve to prevent dispensing of vaporized material proximate to the electrical outlet.

8 Claims, 28 Drawing Sheets

LIQUID VAPORIZATION WITH HOUSING STABILIZATION SYSTEM

FIELD OF THE INVENTION

The present invention relates generally to the field of liquid vaporizers. More specifically, the present invention relates to a method and apparatus for liquid vaporization.

BACKGROUND OF THE INVENTION

Electric liquid vaporizers (often referred to as "liquid electrics") are known. Generally, such electric liquid vaporizers comprise a housing unit configured to receive a liquid container or bottle portion. In such systems, typically the bottle portion includes some type of a wick or wick system which permits the liquid, which is ultimately to be vaporized, to be absorbed therein through capillary action. The housing unit of such a system generally contains a heating mechanism, typically electrically activated. The bottle portion which generally contains the liquid for vaporization, is usually configured for attachment to the housing such that the wick is suitably positioned proximate the heating mechanism so that the liquid will be vaporized. Various systems of the general configuration are known. See for example, U.S. Pat. No. 5,647,053 issued Jul. 8, 1997 to Schroeder et al, U.S. Pat. No. 5,038,394 issued Aug. 6, 1991 to Hasegawa et al, and U.S. Pat. No. 5,290,546 issued Mar. 1, 1994 to Hasegawa et al.

The system disclosed in the '394 and '546 comprises a chemical solution bottle removably fitted into a socket disposed under a heater. The bottle is threaded to fit within the socket in a screw-like manner. In contradistinction, in the system disclosed in the '053 patent a container of volatilizable liquid material is attached to a housing through the use of container attaching means, which means serve to hold the container and wick in place within the housing. The attachment means may include bayonet attachments undercut with matching projections and the like. Other systems which are known include projections contained on the solution bottle for "snap-fit" attachment into the housing. See, for example, U.S. Design Pat. No. 393,063 issued Mar. 31, 1998 to Wefler and U.S. Design Pat. No. 386,974 issued Dec. 2, 1997 to Wefler.

Thus, various methods for connecting bottle portions to housing units have been developed and are known. Typically, such methods comprise simple snap-type mechanisms or screw-thread designs. With such systems, particularly when used in a wick containing vaporizer, the wick may be damaged by being crushed or bent by careless interconnection, or be overheated by contact with the heating element during operation, due to instability and improper positioning of the wick relative to the heating element. This same instability and improper positioning may cause uneven heating of the wick, resulting in diminished evaporative performance and consumer frustration.

In addition, many existing vaporizer units are configured such that the vaporizer's plug structure extends out from the rear of the housing unit a substantial distance. With such vaporizer's, when the unit is plugged into a socket of a wall outlet, because of the extension of the plug structure, excess space between the wall/outlet and the body of the vaporizer is created in the vicinity surrounding the plug structure and the back of the vaporizer housing. Such space may leave the vaporizer susceptible to undesirable movement about the plug structure. The constant weight of the vaporizer unit itself, as well as inadvertent blows to the vaporizer, while the vaporizer is plugged in, may cause the vaporizer to rotate about the plug and potentially cause it to become unplugged from the outlet.

To overcome undesirable movement, some vaporizer designs incorporate a "flush" plug which maintains the body of the vaporizer housing against the wall/electrical outlet in attempts to minimize movement of the inserted vaporizer. However, using a housing that is flush with the wall or outlet presents other problems. For example, because the housing is closer to the electrical socket, the vapor dispensing area of the vaporizer may also be closer to the socket. Likewise, depending on the location of the plug structure, vapor may also be dispensed proximate to the electrical socket. If the vapor condenses the electrical sockets, problems occur.

Lastly, in many buildings, conventional two socket outlets, rather than being vertically oriented, may be oriented in other fashions. For example, the sockets may be horizontal. Thus, when the vaporizer is plugged into the horizontal socket, the vaporizer will likewise be oriented horizontally, thereby reducing the vaporizer's effectiveness and/or potentially causing leakage of the material to be dispensed.

Thus, vaporizer designs which improve upon these and various other aspects are desirable.

SUMMARY OF THE INVENTION

The present invention provides methods and apparatus for securely guiding, centering and stabilizing an electric liquid vaporizer refill bottle in a liquid vaporizer housing unit which addresses many of the shortcomings of the prior art methods and apparatus.

In accordance with one aspect of the invention, a guidance system is provided, wherein guidance of the refill bottle into the housing unit is provided. This guidance system serves to aid in positioning the bottle relative to the housing unit, and in centering the wick relative to the heating element once the parts are interlocked. Preferably, the guidance system comprises one or more ribs and substantially corresponding grooves contained on the refill bottle and/or housing unit. Interlocking of the refill bottle into the housing unit may be achieved with a protrusion on the front of the refill bottle which corresponds to an aperture in the front of the housing unit or in other manners.

In accordance with another aspect of the invention, a bottle stabilization system is provided, wherein stabilization of the combination of the refill bottle and housing is obtained. In general, this stabilization system comprises opposing elements on the refill bottle and/or housing, which elements serve to stabilize the refill bottle relative to the housing.

In accordance with another aspect of the invention, multiple guiding protrusions (ribs) and indentations are provided on the refill bottle and/or housing unit to further facilitate proper guidance of the refill bottle into the housing unit, and to further stabilize and center the refill bottle once it is placed into the housing unit, so that the wick is evenly heated on all sides by the heating element. Further, a guide track may be provided on the housing unit.

In accordance with a further aspect of the invention, additional locking mechanisms are provided on the refill bottle and housing unit to further connect the refill bottle and housing unit. One such connection may be a push-and-release or other type of mechanism to provide child safety protection.

In accordance with yet another aspect of the invention, the bottle unit is shaped to provide easy gripping during the connection and disconnection process, as well as to allow a free flow of air into the housing unit to facilitate evaporation from the wick.

In accordance with the present invention, a liquid vaporizer having a housing stabilization system is provided, wherein stabilization of the housing unit when the housing is inserted into a wall outlet is improved. According to one aspect of the present invention, the stabilization system serves to aid in preventing rotation of the vaporizer about its plug when inserted into a wall outlet.

Preferably, the stabilization system comprises one or more projections contained on the back of the housing unit. The projection is preferably about the same length as the base of the plug of the vaporizer and substantially abuts the wall/outlet when the vaporizer is in place.

In accordance with another aspect of the present invention, the plug structure of the vaporizer is located proximate to a lower portion of the vaporizer. The stabilization system thus can serve to minimize dispensing of the material to be vaporized in the vicinity of the electrical wall outlet into which the dispenser is inserted. For example, when inserted into the lower outlet of a conventional two-outlet electrical wall outlet (e.g., having vertically oriented outlets), the stabilization system covers the upper outlet and/or maintains the dispensing end of the vaporizer away from the wall outlets.

In accordance with still another aspect of the present invention, the plug structure of the vaporizer is rotatable, so that the vaporizer can be maintained in a substantially upright position in wall outlets of various orientations.

In accordance with these and other aspects of the invention, described in greater detail below, the ease of application and performance of an electric liquid vaporizer, as well as its safety, is improved, resulting in greater consistency of product performance, and reduced consumer frustration.

BRIEF DESCRIPTION OF THE DRAWING

Additional aspects of the present invention will become evident upon reviewing the non limiting embodiments described in the following specification and claims taken in conjunction with the accompanying drawing figures, wherein like numerals designate like elements, and:

DETAILED DESCRIPTION OF PREFERRED EXEMPLARY EMBODIMENTS

The following description is of preferred exemplary embodiments only and is not intended to limit the scope, applicability, or configuration of the invention in any way. Rather, the following description merely provides a convenient illustration for implementing a preferred embodiment of invention. For example, various changes may be made in the design and arrangement of the elements described in the preferred embodiments without departing from the scope of the invention as set forth in the appended claims.

Figure 1:
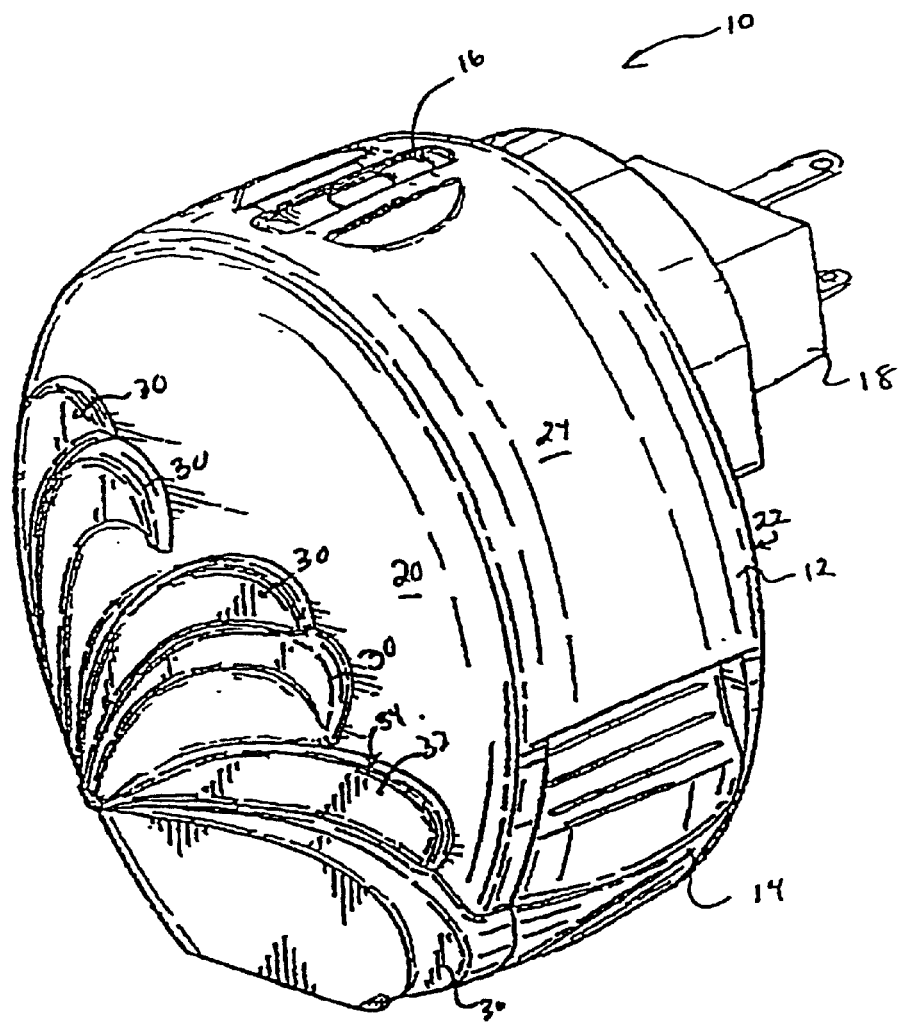
FIG. 1 is a perspective view of a liquid vaporizer in accordance with one aspect of the present invention.

Generally, in accordance with a preferred embodiment of the present invention, a liquid vaporizer system is provided which is configured for enhanced performance. With reference to FIG. 1, a liquid vaporizer system 10 suitably comprises a housing unit 12 and a refill bottle unit 14. As shown, refill bottle unit 14 is suitably configured for disposition within housing 12 and for retention therewithin.

Housing unit 12 suitably includes a vent system 16 and an electrical plug unit 18. In accordance with various aspects of the present invention, electrical plug unit 18 is suitably configured to be inserted into conventional electrical outlets. For example, electrical plug 18 is generally configured as a two prong electrical plug. Of course, electrical plug 18 could likewise be configured in any number of configurations, such as for example, three prong "grounded" plugs, European style plugs or the like.

Figure 19:
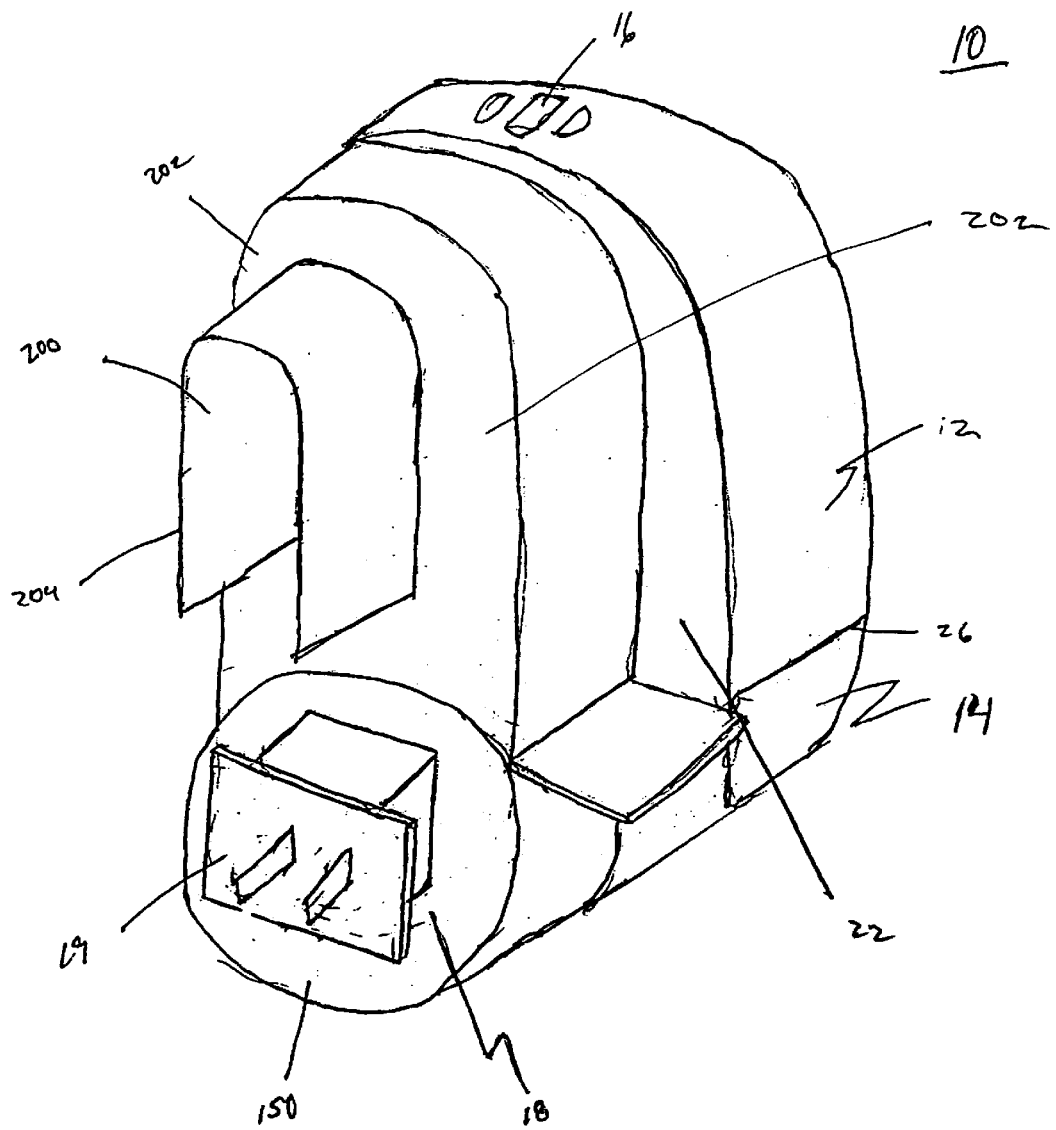
FIG. 19 is a rear perspective view of a liquid vaporizer in accordance with one aspect of the present invention.
Figure 20:
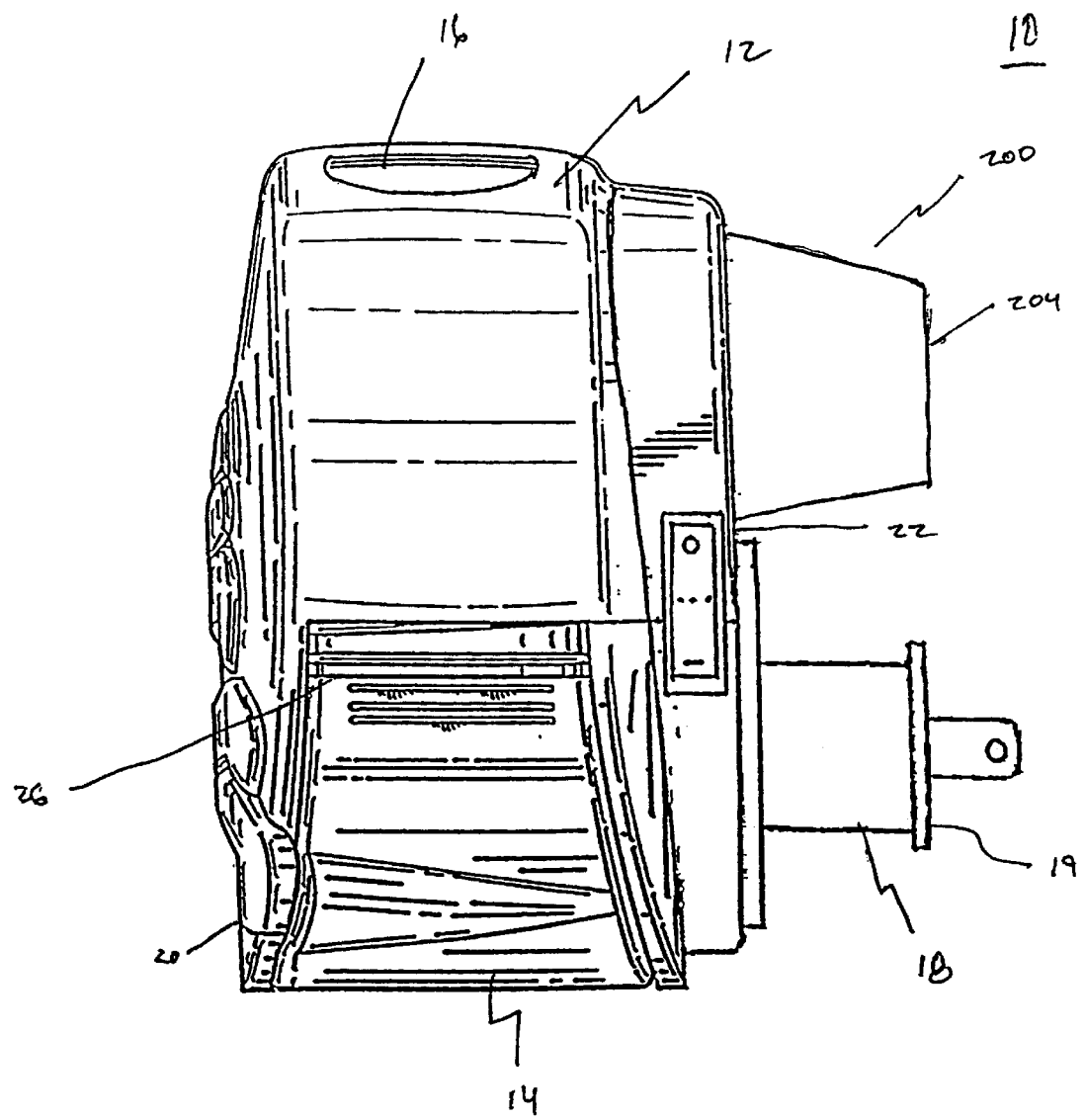
FIG. 20 is a side view of the liquid vaporizer of FIG. 19.
Figure 21:
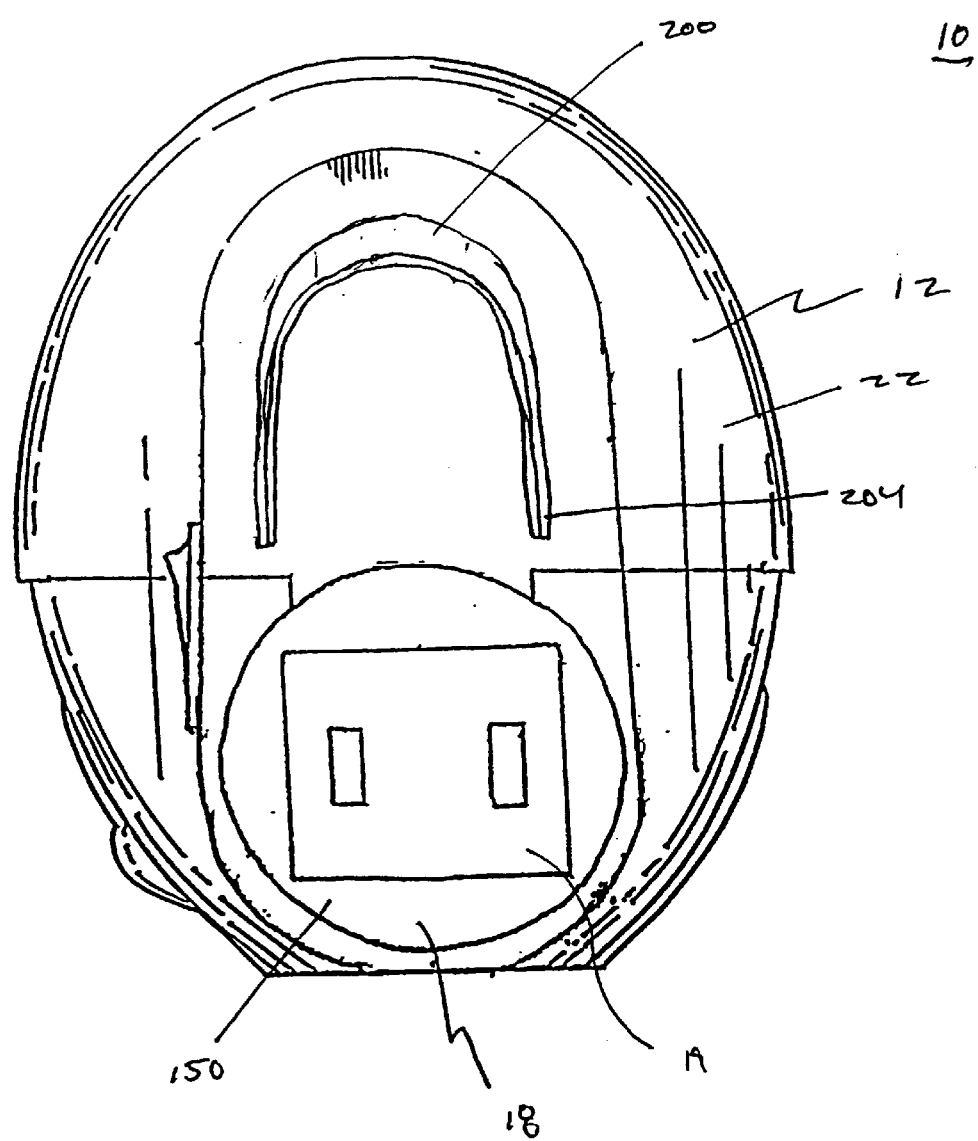
FIG. 21 is a back view of the housing unit shown in FIG. 19.
Figure 22:
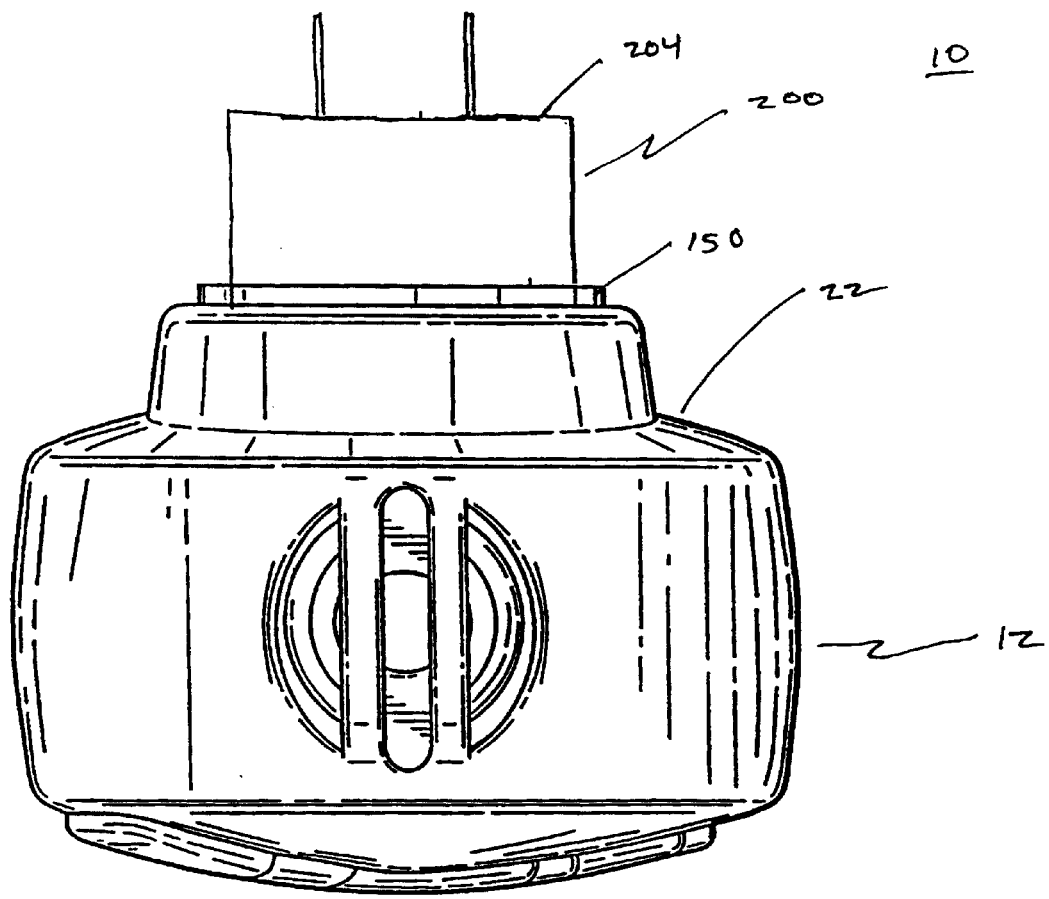
FIG. 22 is a top plan view of the housing unit of FIG. 19.

In accordance with another aspect of the present invention, plug 18 is suitably rotatable with respect to housing 12. For example with reference to FIG. 19, plug 18 is suitably mounted on a rotating disk 150 such that housing 12 may be rotated about plug 18 when vaporizer 10 is inserted into an outlet. Preferably, rotating disk 150 is a substantially circular plate rotatably retained in housing 12 such that housing 12, and thus vaporizer 10, can rotate relative to one another. For example, rotating disk 150 is preferably retained within a groove 152 of housing 12 such that disk 150 is rotatable within groove 152. In accordance with one aspect of the present embodiment, disk 150 comprises one or more projecting stops 154 which suitably abut a retaining projection within groove 152.

In accordance with one aspect of the preferred embodiment, rotating disk 150 is suitably retained such that 360 degree rotation of housing 12 is substantially prevented. For example, in the present exemplary embodiment, housing 12 is rotatable only within a range of 90, 180 and 270 degrees, and preferably, within 90 degrees. Of course, any suitable range of rotation may be employed depending on the particular application of vaporizer 10.

Figure 27:
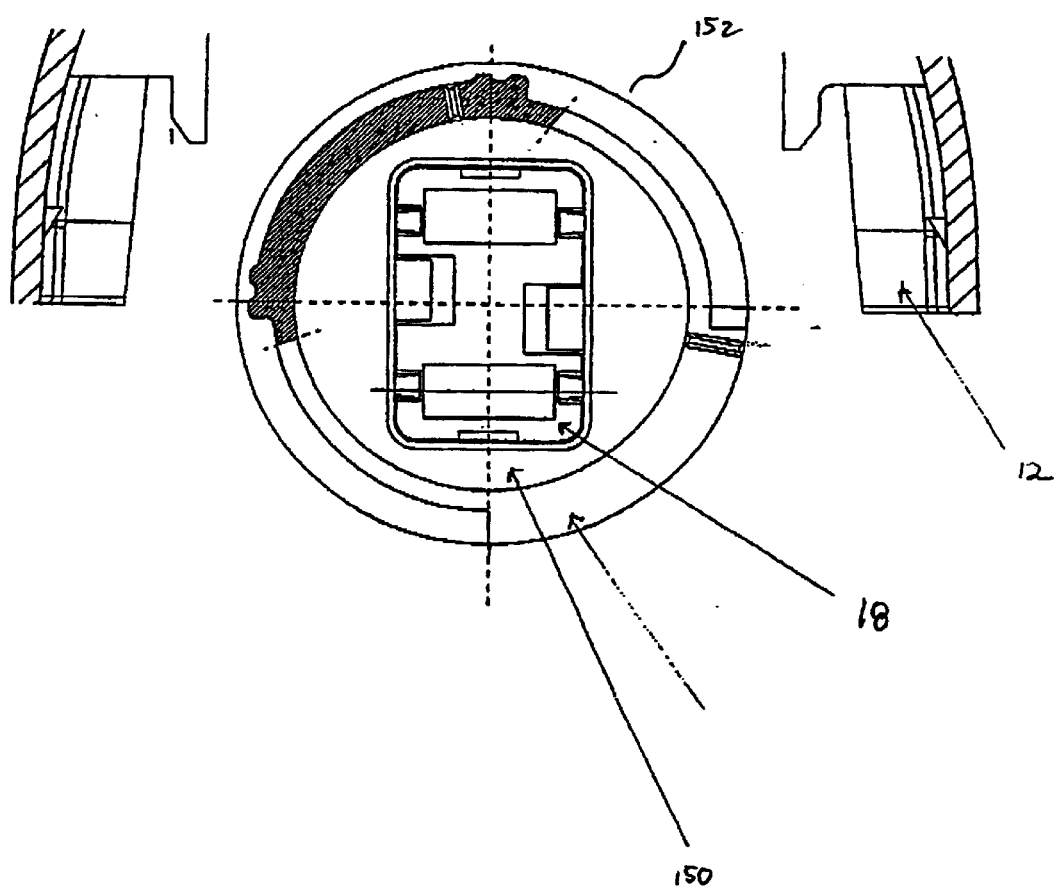
FIG. 27 is a front view of a plug in accordance with an exemplary embodiment of the present invention.
Figure 28:
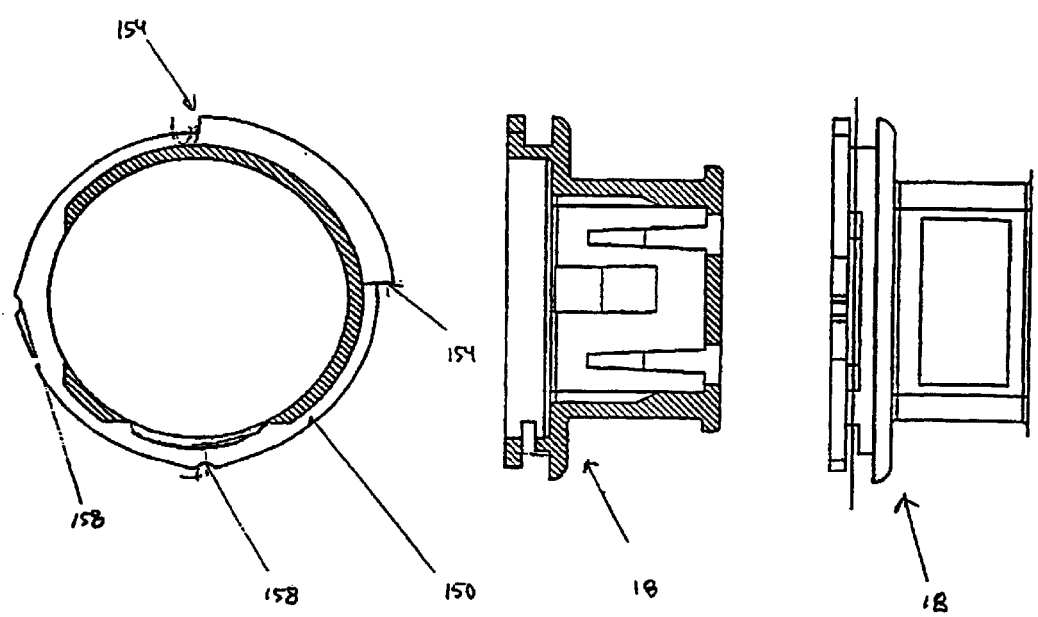
FIGS. 28a,b,c are front, cross-sectional side and side view of a plug in accordance with an exemplary embodiment of the present invention.
Figure 29:
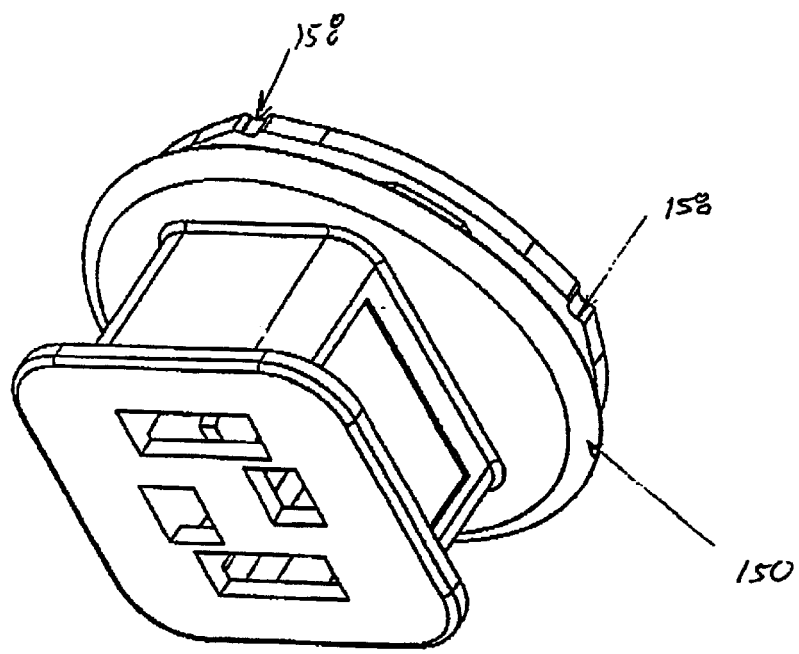
FIGS. 29a,b are perspective views of a plug in accordance with an exemplary embodiment of the present invention.
Figure 29:
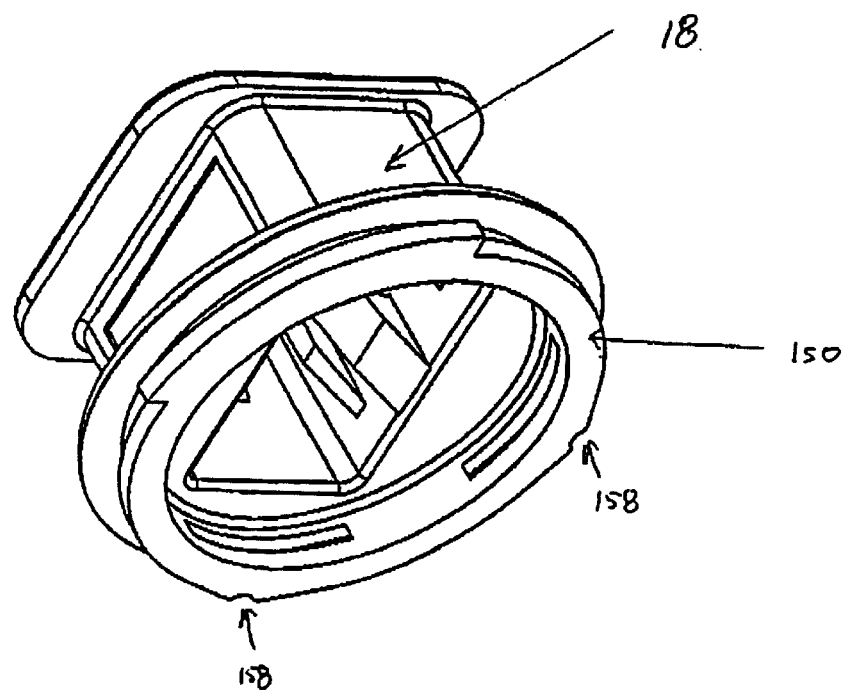

For example with reference to FIG. 28, stop 152 comprises a semi-circular ridge extending throughout about a 90 degree angle on disk 150. Thus, when disk 150 is rotated within groove 152, disk 150 is rotatable until stop 154 abuts retaining projection 156. When disk 150 is rotated in an opposite direction, disk 150 again rotates substantially freely until stop 154 abuts projection 156. Therefore, because stop 154 runs through a 90 degree angle, disk 150 is rotatable through a 270 degree angle. Of course it should be appreciated that any range may be used, for example, by extending stop 154 to encompass 180 degrees, the range of rotation would likewise be 180 degrees. Further still, stop 154 may comprise multiple projecting stops such that rather than having a continuous projection running through a desired range, for example such as that illustrated in the embodiment shown in FIGS. 27–29, stops 154 may comprise a plurality of smaller projections suitably spaced apart bout disk 150 in the desired range of rotation.

In accordance with another aspect of the present invention, one or more locking systems 160 for maintaining disk 150 at a desired position are provided. For example, with continuing reference to FIG. 28, locking system 160 comprises one or more depressions 158 may be provided on disk 150. Depressions 158 are placed on the circumference of disk 150 and engage corresponding projections on housing 12 such that when disk 150 is at a desired position, for example, such that housing 12 is substantially vertical, the projection engages depression 158 and releasably prevents disk 150 from further rotation. Of course, in accordance with various alternative aspects of the invention, various alternative embodiments of locking systems 160 may be used. For example, projections 158 may be located on disk 150, while depressions may be located on housing 12. Similarly, any number of depressions and projection may likewise be employed.

Thus, by limiting the range of rotation, when vaporizer 10 is inserted into a wall outlet which is not oriented vertically (or otherwise), housing 12 can be rotated only to its appropriate upright position, but is restrained from full rotation, thereby preventing vaporizer 10 from being rotated to a canted or upside down position which could cause the material to be dispensed to leak from refill bottle 14 and/or reduce the effectiveness of vaporizer 10. Further, rotation about a full 360 degrees has potential to place stress on vaporizer 10 internal wires, potentially shortening the life of vaporizer 10.

Figure 30:
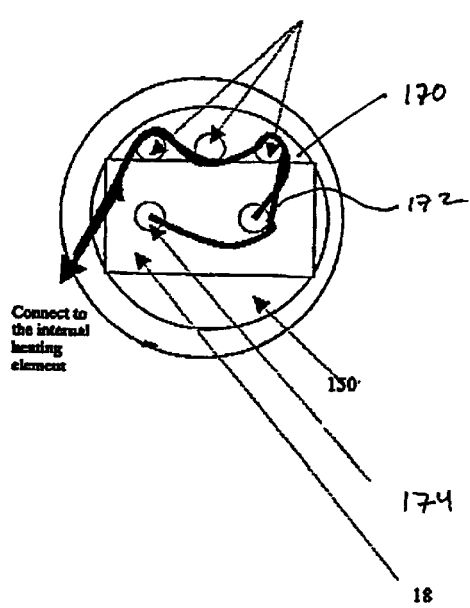
FIG. 30 is a front view of a plug and wiring system in accordance with an exemplary embodiment of the present invention.
Figure 31:
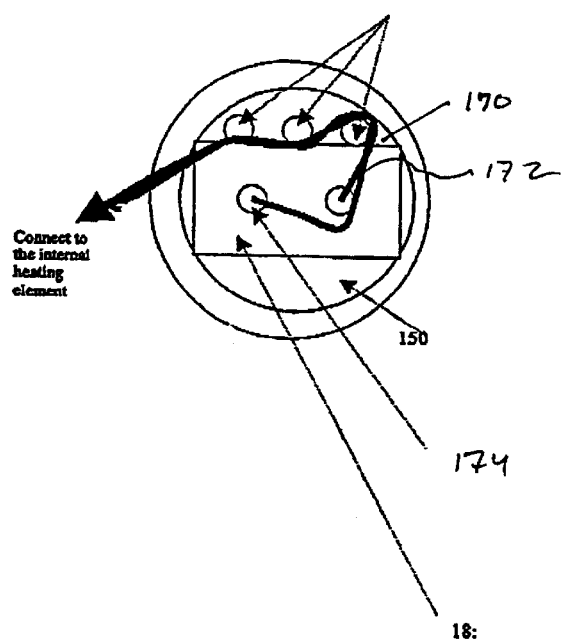
FIG. 31 is a front view of a plug and wiring system in accordance with another embodiment of the present invention.

In accordance with still another aspect of the present invention, a wire locking system 170 which reduces stress placed on the wiring 174 which connects plug 18 and the heating element when plug 18 is rotated is provided. For example, with reference to FIGS. 30–31, wire locking system 170 comprises fixture posts 172 projecting from rotating disk 150 and substantially adjacent to a pin bridge 176 within plug 18. In the present embodiment, wires 174 are maintained between bridge 176 and posts 172. Thus, when plug 18 is rotated, wires 174 rotate with plug 18, thus reducing stress placed on wires 174. In the present preferred embodiment, three posts are 172a,b,c are provided. With reference in particular to FIG. 30, the three posts 172a,b,c are aligned parallel to bridge 176. Wires 174 are intertwined with posts 172a, b, c such that wires 174 are "pinched" between bridge 176 and middle post 172b, yet extend about and/or around outer posts 172a,c. Thus, wire locking system 170 aids in reducing rotation of wires 174 about their respect contact points, and thus help reduce breaking of wires 174.

Of course, any number of posts or other clasping mechanisms may also be used. For example, loops which wire 174 passes through, electrical clasps, and the like may also be used to maintain wires 174 in a secured manner. Likewise, wires 174 may also be "pinched" and/or held by and between any combination of the foregoing. For example, with reference to FIG. 31, wires may be clasped by one outer post 172a and a middle post 172b, but not the other outer post 172c.

Bottle unit 14 is configured for receipt of a vaporizable liquid material. In accordance with various aspects of the present invention, the vaporizable material can be any number of conventional materials dispensed from vapor dispensers including fragrances, disinfectants, sanitizing agents, insect repellents, insecticides and the like. Preferably, and in accordance with a preferred aspect of the present invention, the material to be volatilized comprises a fragrance material and system 10 is used as a air freshening device. In this manner, refill bottle unit 14 is suitably filled with a fragrance containing material and is inserted into housing unit 12 such that the fragrance material can be vaporized through operation of a heater unit which promotes or encourages vaporization from the wick. The vaporized fragrance passes through vent system 16 to the environment.

Inasmuch as the operation of liquid vaporizers of this type is generally known to those of skill in the art, the operation will not be described in detail herein. Suffice it to say, however, that in accordance with various aspects of a preferred embodiment of the present invention, electrical plug unit 18 is plugged into a conventional electrical outlet thereby causing a heater unit to heat the liquid and vaporized liquid which have been drawn up into the wick and allow the same to escape through the openings in vent system 16. The term "vaporized" as used herein is used in a conventional sense and is intended to include not only the formation of vapors but also the formation of small aerosol sized particles which, as is known in the art, may be generated by actuation of such device.

While any heater unit may be used, preferably the heating unit comprises a heating element which can be readily and reliably charged through use in a conventional outlet. In such a manner, heating element (not shown) is electrically connected to plug unit 18. In accordance with a preferred aspect of the invention, the heater unit is of the type described in PCT Application No. 97/00157, filed Jun. 18, 1997 by DBK Espana S. A., published Dec. 23, 1998, the subject matter of which is hereby incorporated herein by reference. However, other heating units may be utilized, as will be readily recognized by those skilled in the art. Similarly, and as is generally shown in the various figures, plug unit 18 may be any conventional plug unit and may be oriented in any particular direction, or even configured for rotation within housing unit 12.

Figure 2:
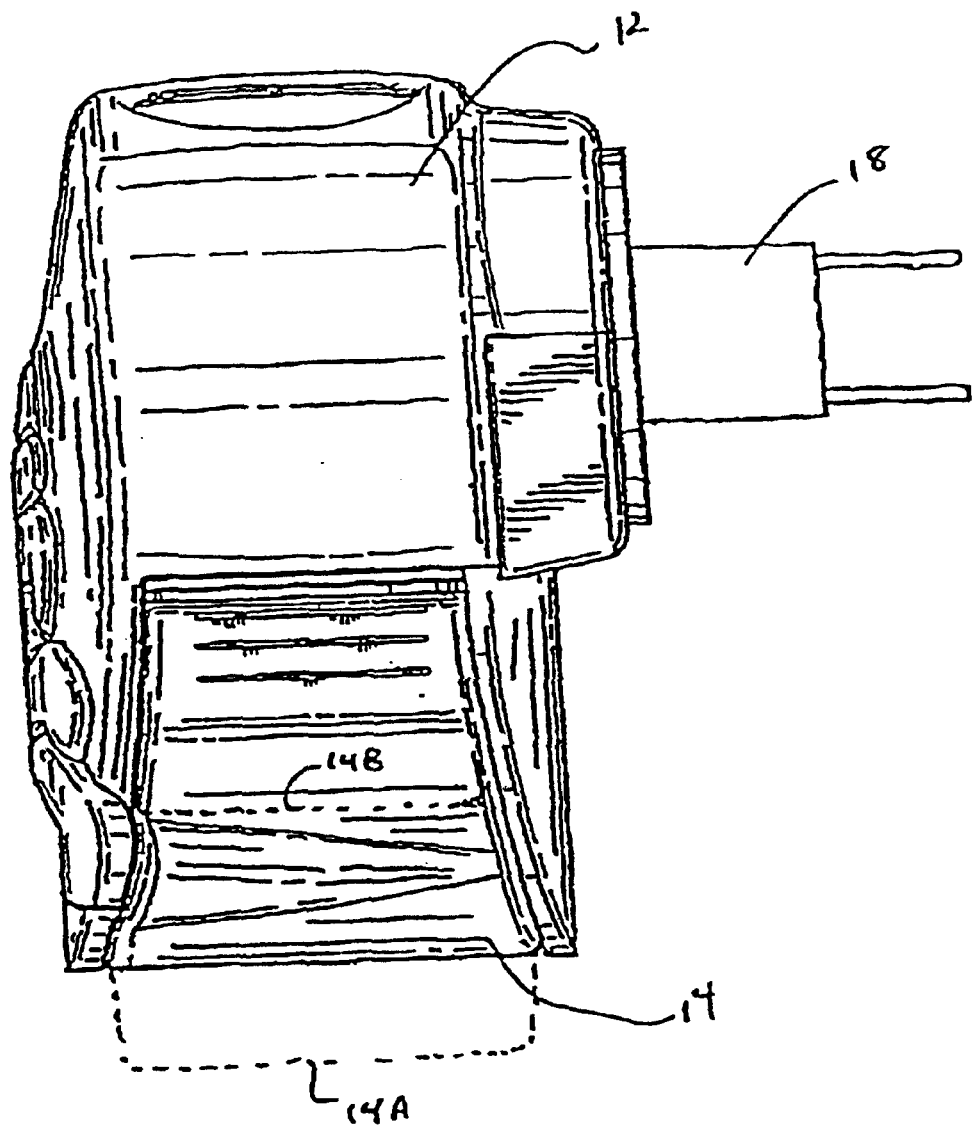
FIG. 2 is a side view of the liquid vaporizer of FIG. 1.
Figure 4:
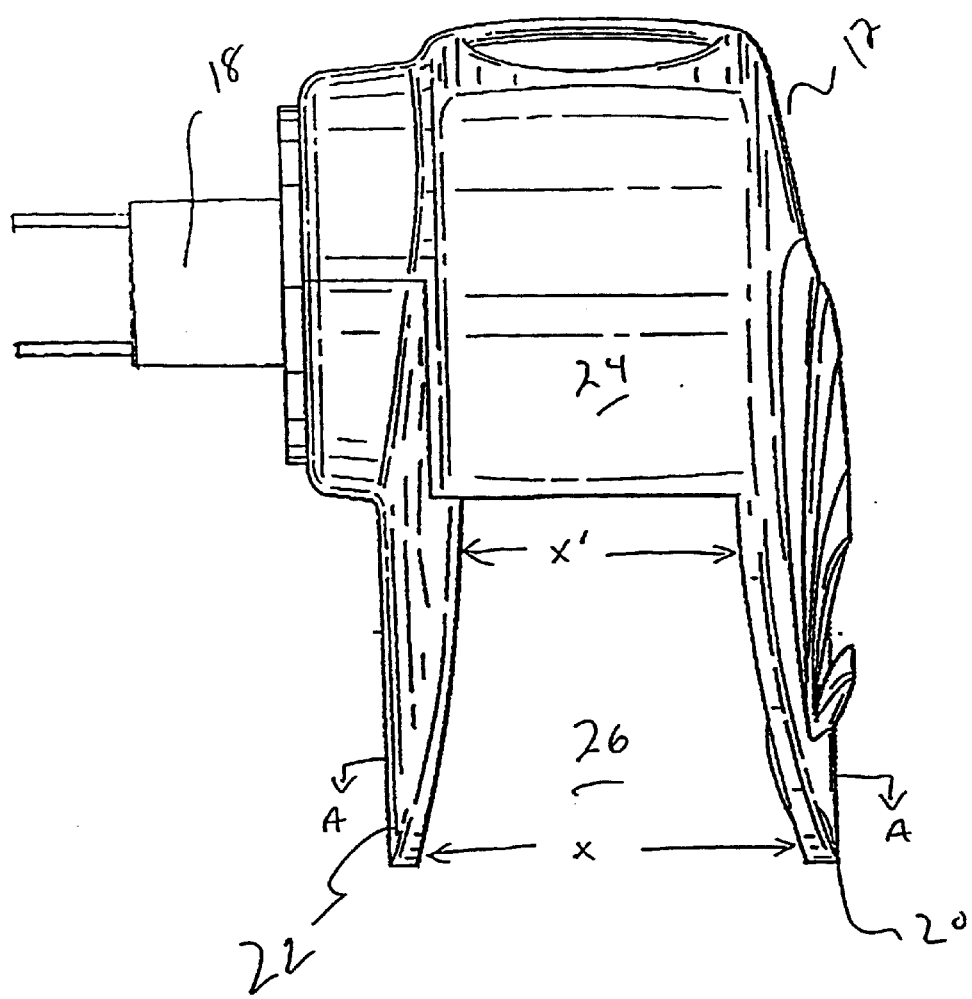
FIG. 4 is a side view of the housing unit shown in, for example, FIG. 3.
Figure 5:
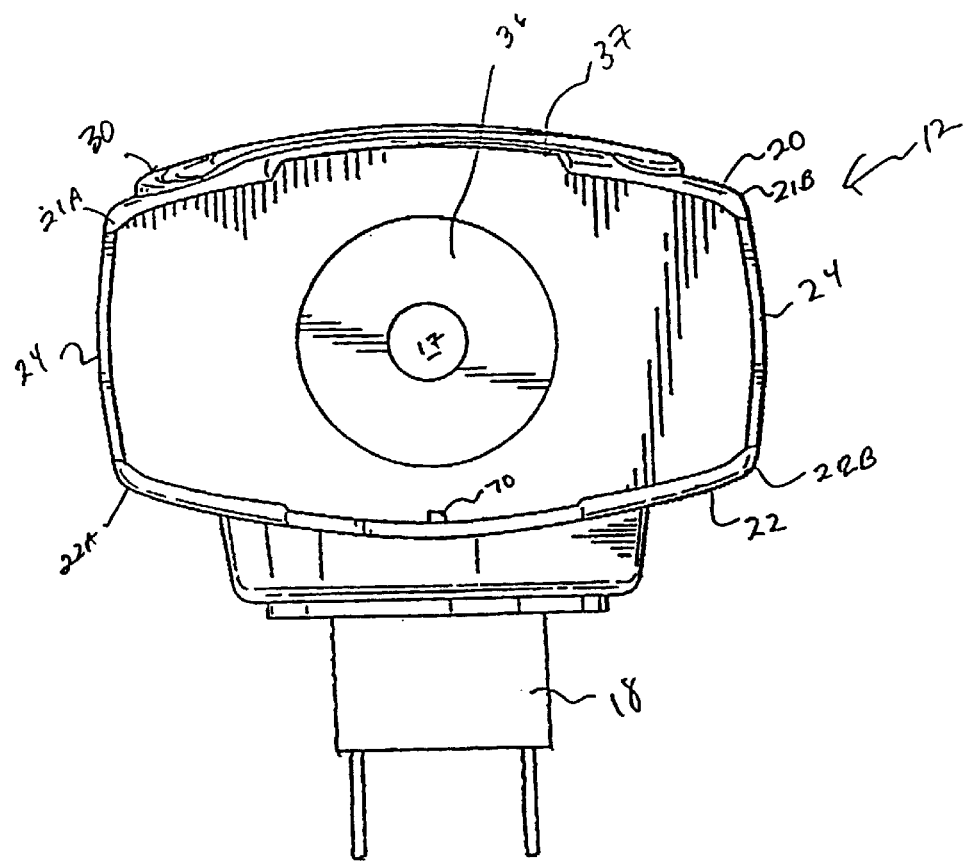
FIG. 5 is a bottom plan view of the housing unit of FIG. 4.

With continued reference to FIG. 1, and with further reference to FIGS. 2 and 5, housing unit 12 is configured to include a housing front surface 20, a housing back surface 22 and an interconnecting top surface 24. Preferably, as shown best in FIGS. 2, 4 and 5, housing unit 12 is configured with a partially open bottom 26 which is configured for receipt of refill bottle unit 14.

With continued reference to FIG. 1, front surface 20 of housing unit 12 suitably is provided with a decorative element. As will be described in greater detail hereinbelow, preferably refill bottle unit 14 and housing unit 12 are interconnected in a "snap-and-fit" manner and preferably the design element contained on front housing 20 is suitably configured for such purposes. That is, preferably an element on bottle unit 14 is suitably configured to cooperate with a portion of housing front wall 20 to provide the "snap-and-fit" configuration and thus, interconnect bottle unit 14 and housing unit 12. In this regard, and with momentary reference to FIG. 3, preferably front housing surface 20 is configured with a plurality of decorative shapes 30 and with an opening 34 for receipt of a substantially corresponding shape 32 contained on bottle unit 14. Preferably, element 32 contained on bottle unit 14 is in a raised or projected fashion for receipt within substantially corresponding aperture 34 contained on or within front surface 20 of housing unit 12. It will be appreciated by those skilled in the art that various projection configurations may be utilized to enable bottle unit 14 to be interconnected with housing unit 12 and the configuration set forth in the drawing figures is for illustrative purposes only. For example, element 32 may be smaller than aperture 34, or comprise multiple geometric configurations. Other configurations now known or hereafter devised by those skilled in the art may also be used. However, as will be discussed in greater detail hereinbelow, in accordance with various aspects of the present invention, a bottle stabilization system is provided in which the interconnection between refill bottle unit 14 and housing unit 12 is stabilized through the provision of suitably configured and arranged elements either on refill bottle unit 14 and/or housing 12.

As shown, for example, in FIGS. 1 and 2, preferably, housing unit 12 and refill bottle unit 14 fit together to provide a uniform profile system 10. However, it should be appreciated in accordance with various embodiments of the present invention, refill bottle 14 may be suitably configured to be larger than housing unit 12, such as is shown by the phantom line 14A of FIG. 2, or alternatively smaller than housing unit 12, such as is shown by the phantom line 14B of FIG. 2. With momentary reference to FIGS. 16 and 17, refill bottle 14 may be configured to extend beyond housing 12, as is illustrated therein, or in any other shape as is now known or hereafter devised by those skilled in the art.

Figure 3:
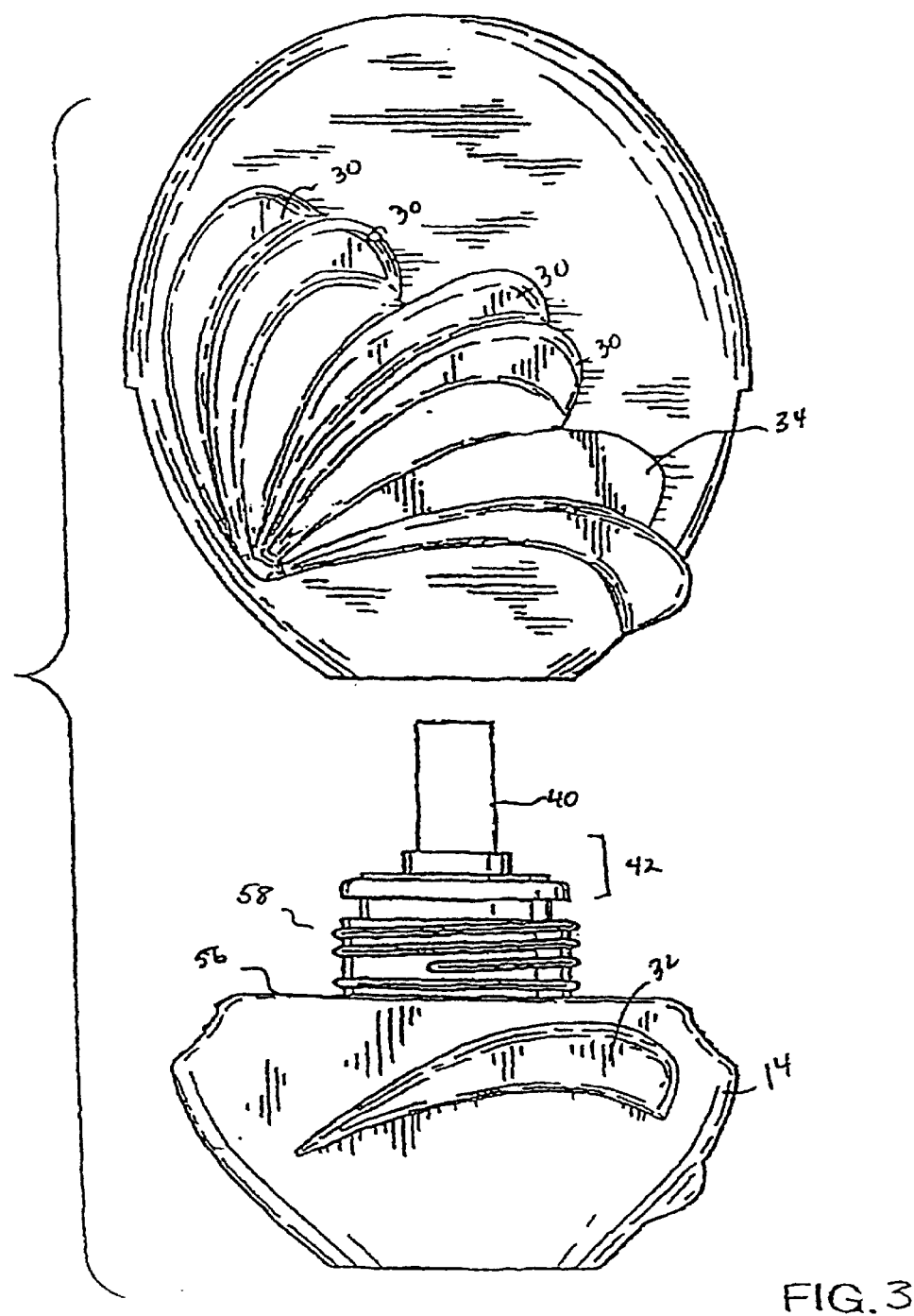
FIG. 3 is an exploded front view of the liquid vaporizer of FIG. 1, showing a bottle unit and a housing unit which comprise the liquid vaporizer.
Figure 11:
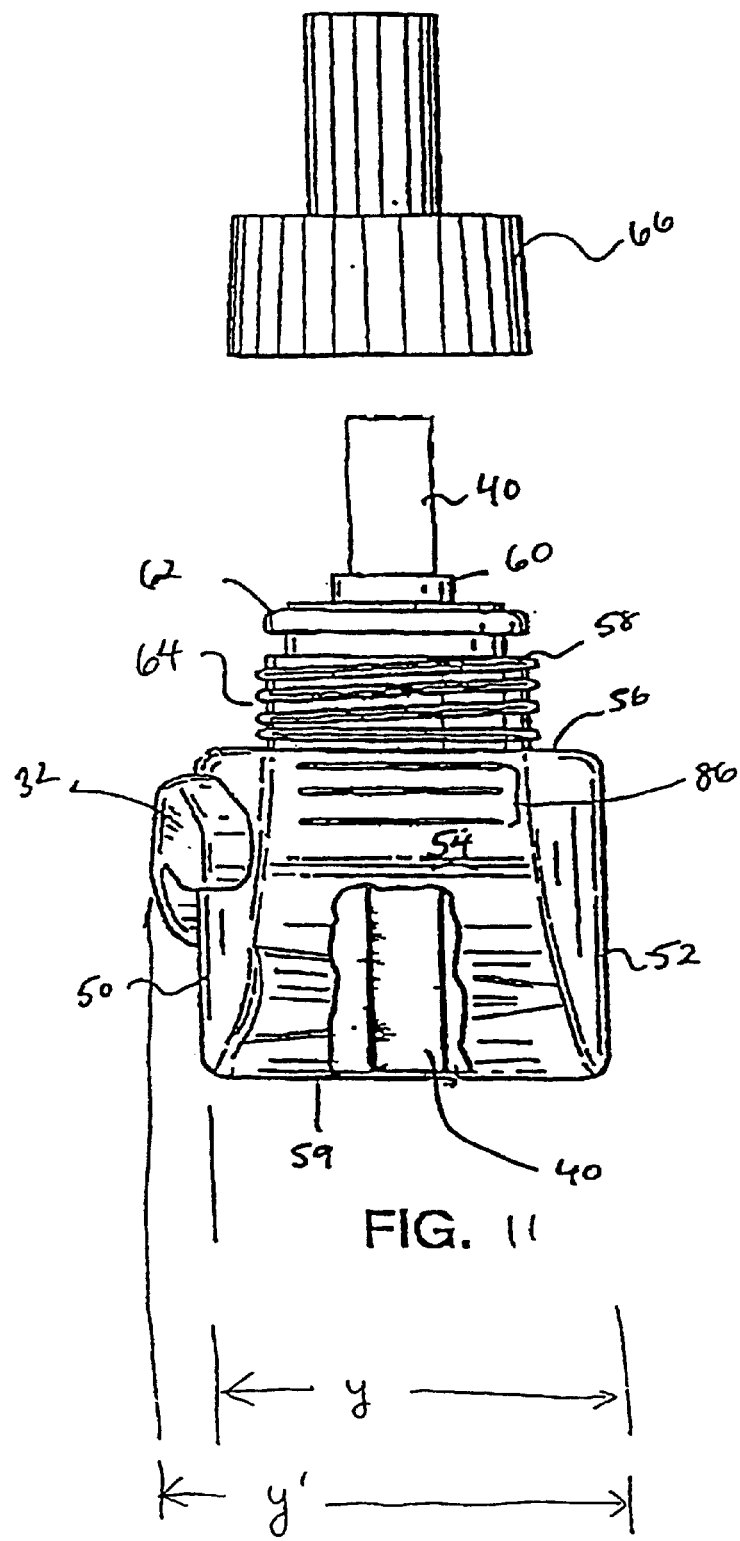
FIG. 11 is a side sectional view of the bottle unit of FIG. 2.

With reference now to FIGS. 3 and 11, refill bottle 14 preferably includes a front wall 50, a back wall 52 and a continuous side wall 54 spanning therebetween. Side wall 54 preferably terminates in a top 56 which communicates with a neck 58. Side wall 54 further provides a bottom 59 which is suitably flat such that bottle unit 14 may be rested upon a flat surface. Alternatively, other configurations and curved or arcuate surfaces forming bottom 59 of refill 14 may be employed. As previously briefly noted, front surface 50 of bottle 14 preferably includes a projection 32 configured for receipt in a suitably configured aperture 34 formed in front surface 20 of housing 14.

Preferably, bottle 14 is suitably sized for use in connection with household use. In accordance with various aspects of the present invention, bottle 14 preferably is configured for receipt of between about 25 to about 75 milliliters of liquid material, more preferably from about 35 to about 50 milliliters of liquid. With reference to FIG. 11, bottle 14 preferably has a width Y about its axis, which when inclusive of element 32 has a width Y'. Preferably, Y is between about 30 and about 40 millimeters, more preferably between about 33 and about 36 millimeters, and Y' is on the order of about 35 to about 45 millimeters, more preferably on the order of about 38 to about 39 millimeters. In this regard, preferably system 10 has suitable weight and dimension to be compliant with various UL (Underwriters Laboratories) guidelines applicable to direct plug-in devices. For example, the weight and moment of the device/system inclusive of the refill bottle is such that the center of gravity is appropriately positioned and the weight is less than that which would otherwise cause the device/system to be unstable within the outlet.

Preferably, refill bottle 14 is a conventional bottle or similar device configured to receive a volatilizable material and hold a wick 40 firmly in place. Generally, wick 40 will be secured to refill bottle 14 by a wick securement system 42. Wick securement system 42 preferably includes a wick retaining element 60 and an attachment ring 62. Preferably, wick 40 is secured within wick retainer 60 which in turn is attached to attachment ring 62 which is crimped or otherwise attached to neck 58 of refill bottle 14.

Neck 58, as shown, for example, in FIG. 11, is preferably threaded and thus includes a plurality of threads 64. Threads 64 are suitably configured to receive a cap 66 for securing refill bottle 14 prior to use. Preferably, as shown best in FIG. 11, wick 40 extends substantially to the bottom 59 of refill bottle 14.

Preferably, refill bottle 14 and cap 66 comprise a plastic material which is compatible with the material to be vaporized. For example, refill bottle 14 may be formed of polypropylene (which may be clarified), barex and/or PET. Similarly, housing 12 suitably comprises a plastic material, such as polypropylene or high-density polyethylene. However, in certain applications, it may be desirable for bottle 14 to be formed of other materials such as glass or the like. In accordance with various aspects of the present invention, wick securement system 42 may suitably comprise of plastic, metal or other materials. It should be appreciated that the particular composition of refill bottle 14, cap 66, securement system 42 and/or housing 12 may be modified to any material composition as is now known or hereafter devised by those skilled in the art.

Wick 40 may be formed from any conventional wick material. Suitable wick materials include porous/sintered plastics such as high density polyethylene and polypropylene, bonded fibers, glass sintered fibers, ceramic materials, carbon fibers, sintered carbon, wood, compressed wood composites bundled or woven material fibers, bundled or manmade fibers. In general, wick 40 can be formed of any suitable material now known or hereafter devised by those skilled in the art.

In addition, wick 40 may be provided with a sheath. However, as will be described in greater detail hereinbelow, through use of the present invention, sheathing the wick for protection during use is not necessary. For example, in many of the prior art configurations, wicks, like wick 40, are provided with a sheath which serves to protect and stabilize the wick and prevent interaction between the wick and the heating unit used in volatilizing the material absorbed therein. In particular, in certain prior art units, particular prior art "snap-and-fit" units wherein the refill bottle container is snapped into the housing unit, suffer from the disadvantage that the refill bottle unit and housing unit wobble or move with respect to one another. Such wobbling can cause the wick material to interact, perhaps in a deleterious and/or disadvantageous manner with the heating unit during use. To prevent such deleterious effects, in general, prior art users have sheathed the wick to prevent and protect it from contact with the heater unit.

In accordance with various aspects of the present invention, the interaction between refill bottle unit 14 and housing unit 12 is enhanced through provision of a guidance system. Further, the system is enhanced by stabilizing the bottle through the provision of a stabilization system.

In general, the guidance system in accordance with various aspects of the present invention may include any mechanism or combination of mechanisms which serve to guide refill bottle unit 14 with respect to housing unit 12 when refill bottle unit 14 is inserted into housing unit 12. Preferably, in accordance with various aspects of the present invention, the guidance system comprises one or more protrusions contained in or on the inside surface of back wall 22 of housing unit 12 which correspond with grooves or indentations in or on the back surface 52 of refill bottle unit 14. Further, the guidance system may include a track provided in front wall 20 of housing 12. It should be appreciated, however, that other configurations which serve to guide refill bottle unit 14 with respect to housing unit 12 as may hereafter be devised by those skilled in the art in light of the foregoing and following description may also be utilized.

As briefly noted above, and as will be described in greater detail herein below, preferably bottle 14 and housing unit 12 are secured through a "snap-and-fit" arrangement. While such "snap-and-fit" arrangements are generally known, such arrangements suffer in that the bottle tends to not be readily stabilized within the housing unit 12. In accordance with various aspects of the present invention, a stabilization system is provided which serves to stabilize refill bottle unit 14 with respect to housing unit 12 when refill bottle unit 14 is inserted into housing unit 12. Preferably, in accordance with various aspects of the present invention, the bottle stabilization system can include any mechanism or combination of mechanisms which serve to so stabilize refill bottle unit 14 with respect to housing unit 12. However, preferably, the bottle stabilization system in accordance with the present invention includes securement mechanisms located on bottle unit 14 and housing unit 12 along opposing axes of bottle unit 14. For example, such bottle stabilization and stabilization of bottle 14 with respect to housing 12 may be provided through provisions of the aforementioned guidance system together with the "snap-and-fit" arrangement, such as provided by projecting element 32 received with an aperture 34. Alternatively, various other bottle stabilization systems, as will be hereinafter described, can be utilized to enhance stabilization of refill bottle unit 14 with respect to housing unit 12.

Figure 6:
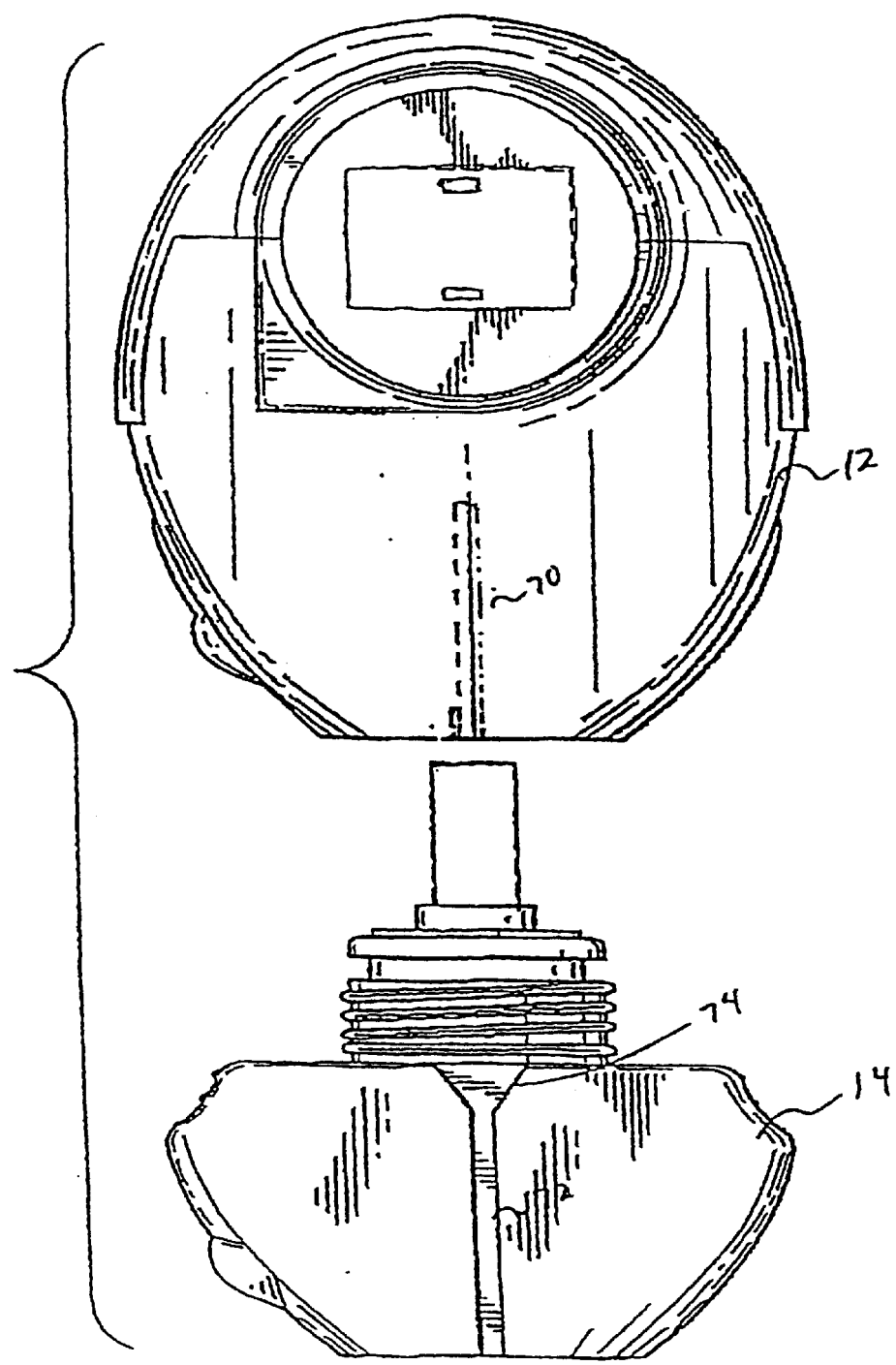
FIG. 6 is an exploded view of a liquid vaporizer, similar to that of FIG. 3, but instead showing the back view of each of the housing unit and the bottle unit.
Figure 7:
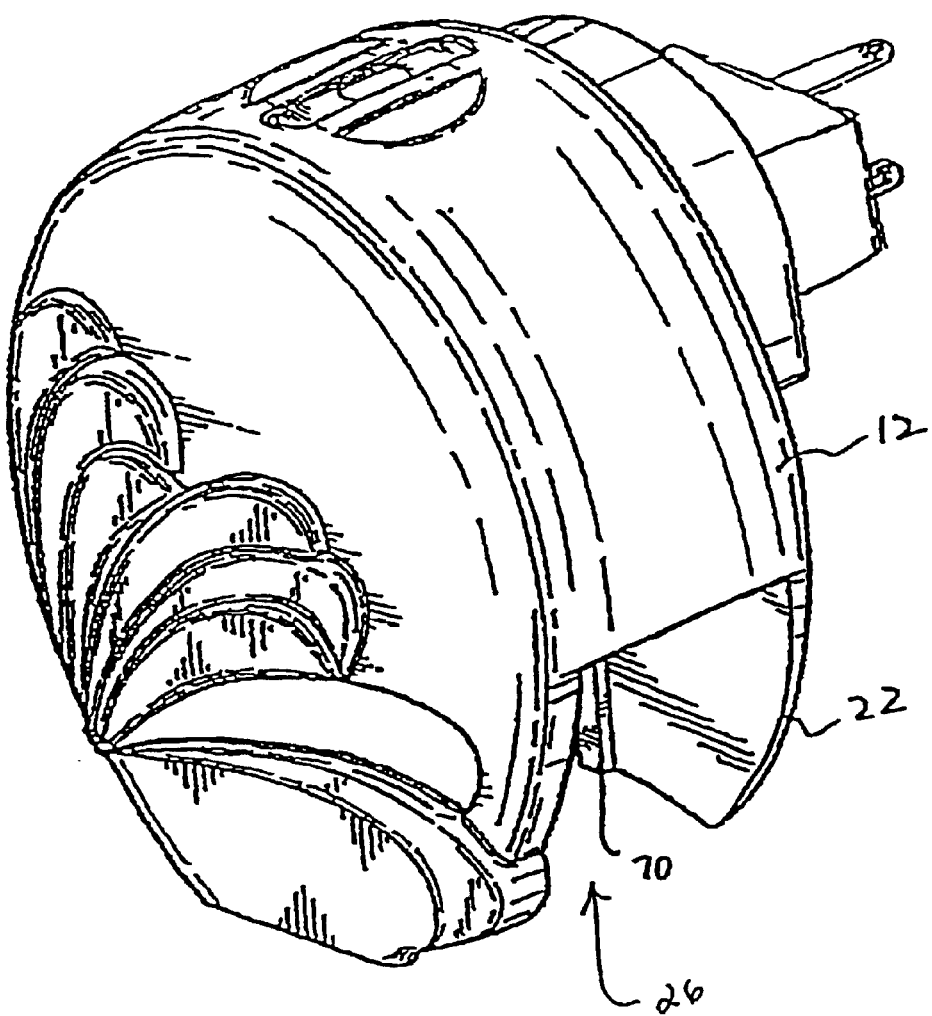
FIG. 7 is a perspective view of the housing unit shown in FIGS. 3 and 4.
Figure 10:
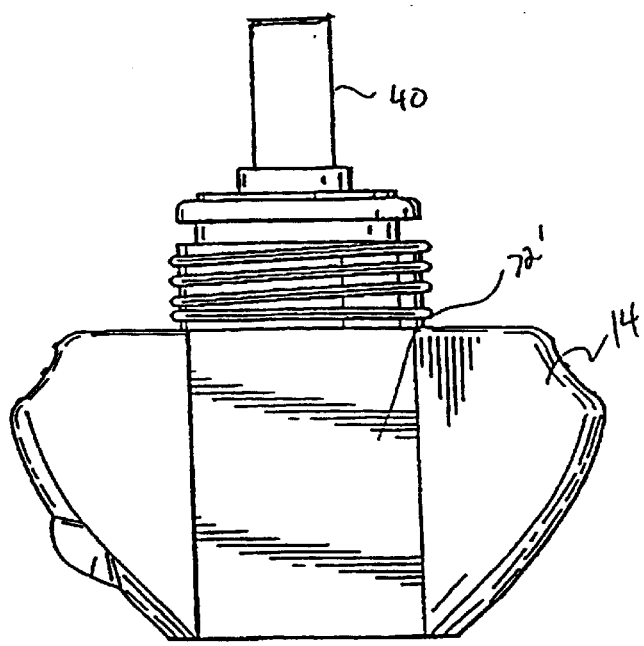
FIG. 10 is a back view of a further alternative embodiment of a bottle unit useful in accordance with the present invention.

With reference to FIGS. 6 and 7, a guidance system in accordance with one preferred exemplary embodiment of the present invention will now be described. In accordance with this embodiment of the present invention, the inside surface or back surface 22 of housing unit 12 is provided with an outwardly extending projection 70. Projection 70 is suitably placed about the center line of back surface 22, however other placements can be employed. Similarly, a substantially corresponding recess 72 is suitably formed in back wall 52 of refill bottle 14. As shown best in FIG. 4, recess 72 preferably has an enlarged upper opening 74 which aids in alignment of protrusion 70 into the lower portion of recess 72. While the guidance system thus illustrated comprises an indentation or groove on refill bottle 14 which corresponds with a protrusion or projection on housing unit 70, it should be understood that the protrusion could be positioned on refill bottle 14 and the corresponding groove on housing 12.

Projection 70 preferably extends a length which generally corresponds to the length of groove 72, which in turn generally spans the height of bottle unit 14. However, projection 70 may be configured longer or shorter as may be desired for any particular application. Moreover, although groove 72 is shown as being substantially open at is top end and bottom end, in certain applications it may be desirable to close the top end of groove 72.

Figure 8:
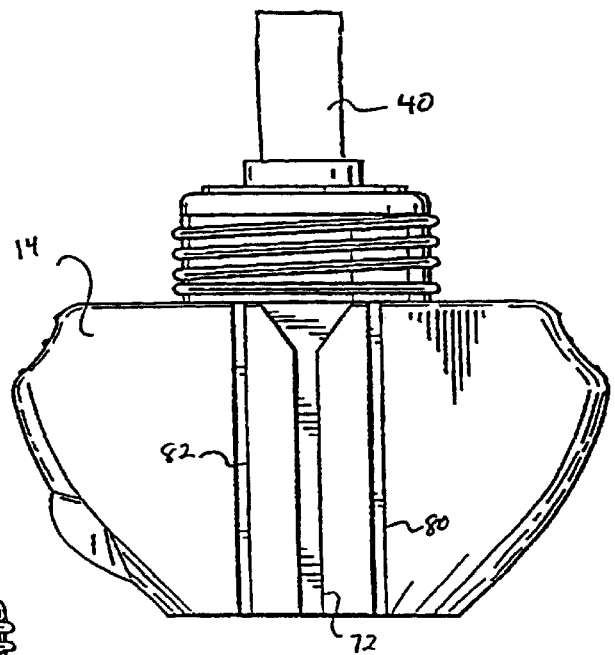
FIG. 8 is a back view of an alternative embodiment of a bottle unit useful in accordance with the present invention.
Figure 9:
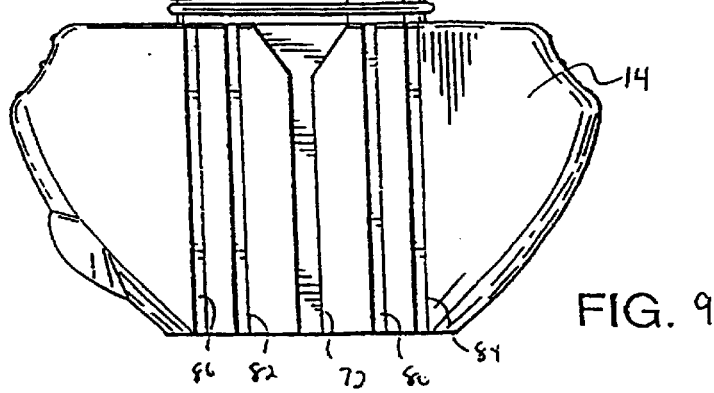
FIG. 9 is a back view of a further embodiment of a bottle unit useful in accordance with the present invention.

It should be appreciated that various numbers of grooves and/or indentations or combinations thereof may be utilized in accordance with various aspects of the present invention. With reference now to FIGS. 8–10 and 12–15, further embodiments of guidance systems useful in accordance with the present invention are shown. For example, referring now to FIG. 8, in addition to central recess 72, respective secondary recesses 80 and 82 are also provided. It should be appreciated, further support can be obtained through utilization of a plurality of protrusions and corresponding grooves. For example, with reference to FIG. 9, a further embodiment comprises central recess 72, secondary grooves and 82 and tertiary grooves 84 and 86. As shown in FIGS. 8 and 9, secondary and tertiary grooves are suitably configured to have a width narrower than the width of central groove 72. Accordingly, the corresponding projections contained on back wall 22 of housing unit 12 are similarly configured. For example, with momentary reference to FIG. 15, a projection pattern which generally corresponds to the groove pattern shown on refill bottle 14 in FIG. 9 is shown as being formed on back surface 22 of housing unit 12.

Although not shown, various other combinations of grooves and/or indentations contained on one or both of refill bottle unit 14 and/or housing unit 12 can be formed. For example, in the embodiment shown in FIGS. 17 and 18, instead of tertiary grooves 84 and 86 being formed on bottle unit 14, such grooves may be replaced with projections which correspond to grooves suitably aligned on refill housing back wall 22. Alternatively, and with momentary reference to FIG. 10, a single groove 72' may be formed on bottle 14. Groove 72' may be mated with a corresponding projection on back surface 22 of housing unit 12, or in certain instances with a projection pattern of the same width or less than the width of the groove 72'. For example, projection patterns formed on the inside of housing back wall 22 corresponding to the groove patterns shown in FIGS. 6, 8 and 9 could suitably be used in connection with the bottle shown in FIG. 10.

The guidance system in accordance with various aspects of the present invention may also include a track within front surface 20 of housing unit 12. With reference now to FIG. 5, housing unit 12 is suitably provided with wick receiving aperture 17 which is centrally located within bottle receiving region 36. Preferably, as shown best in FIGS. 4 and 5, walls 20 and 22 of housing unit 12 suitably extend downwardly from the major portion of housing unit 12 and regions 17 and 36. Preferably, and in accordance with various aspects of the present invention, front wall 20 of housing unit 12 is suitably provided with a guide track 37 which serves to orient refill bottle 14 within housing unit 12 when refill bottle unit 14 is inserted therein. Preferably, guide track 37 is suitably configured for receipt of element 32. That is, element 32 and guide track 37 are suitably proportioned such that when bottle 14 is inserted within housing unit 12, element 32 generally corresponds to and is guided within track 37. Of course, various other configurations may be utilized to accomplish this further aspect of the present invention. For example, decorative elements other than the elements shown in FIG. 3 may be utilized. It should also be appreciated that in certain applications it may not be necessary to utilize front track 37 to aid in the insertion of refill bottle 14 into housing unit 12.

Figure 12:
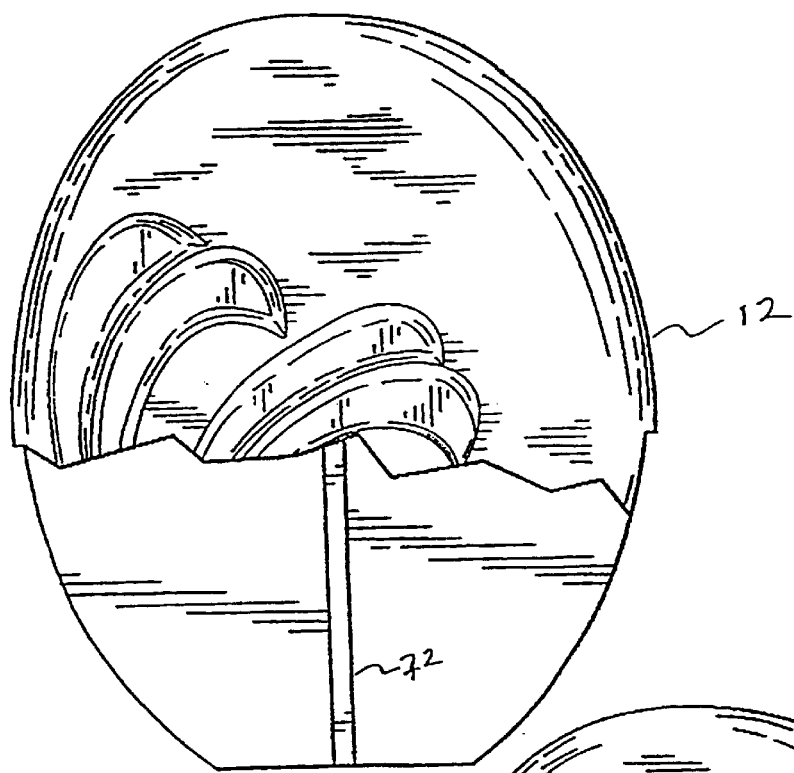
FIG. 12 is a front partial sectional view of the housing, for example such as is shown in FIG. 7.
Figure 13:
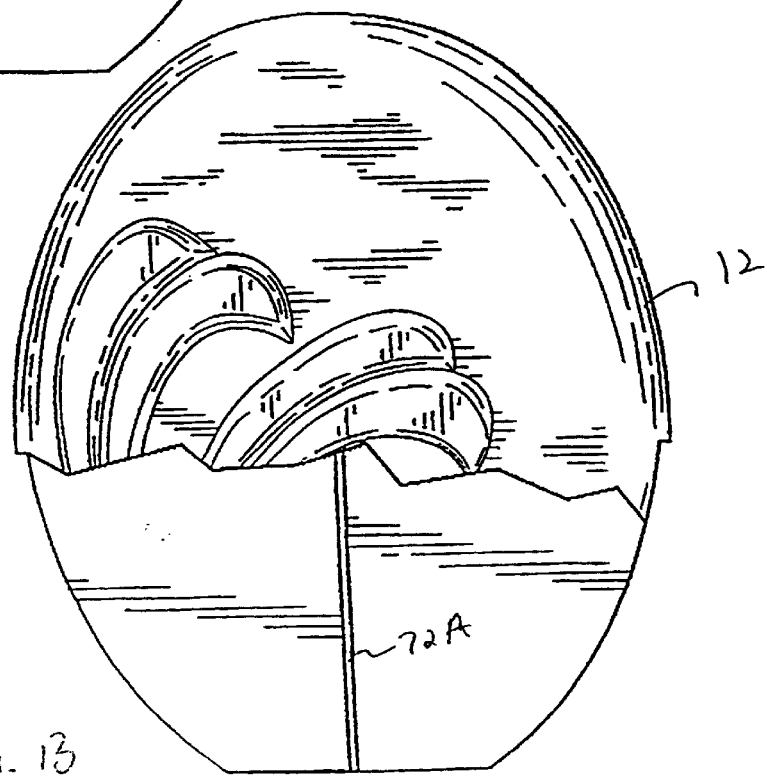
FIG. 13 is a front partial sectional view of an alternative embodiment of a housing useful in accordance with the present invention.
Figure 14:
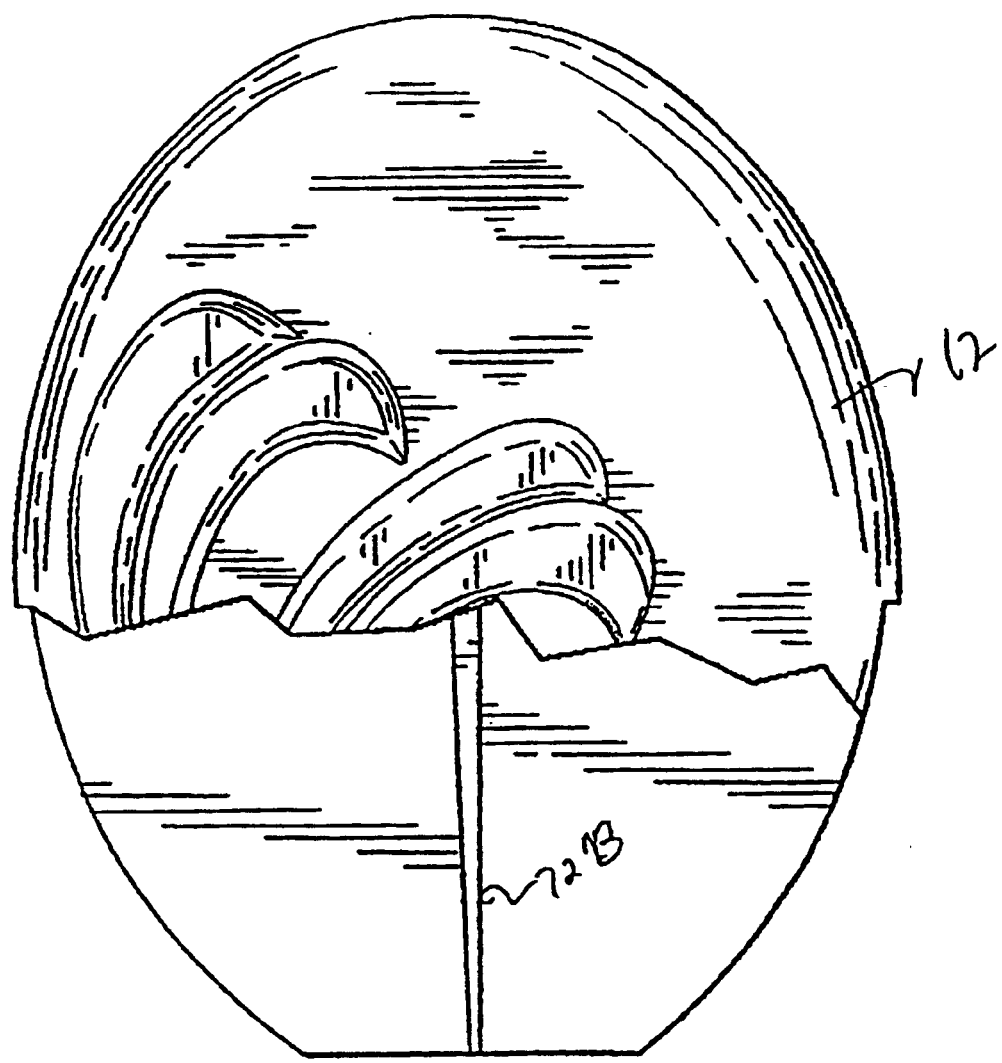
FIG. 14 is a front partial sectional view of a further embodiment of a housing useful in accordance with the present invention.
Figure 15:
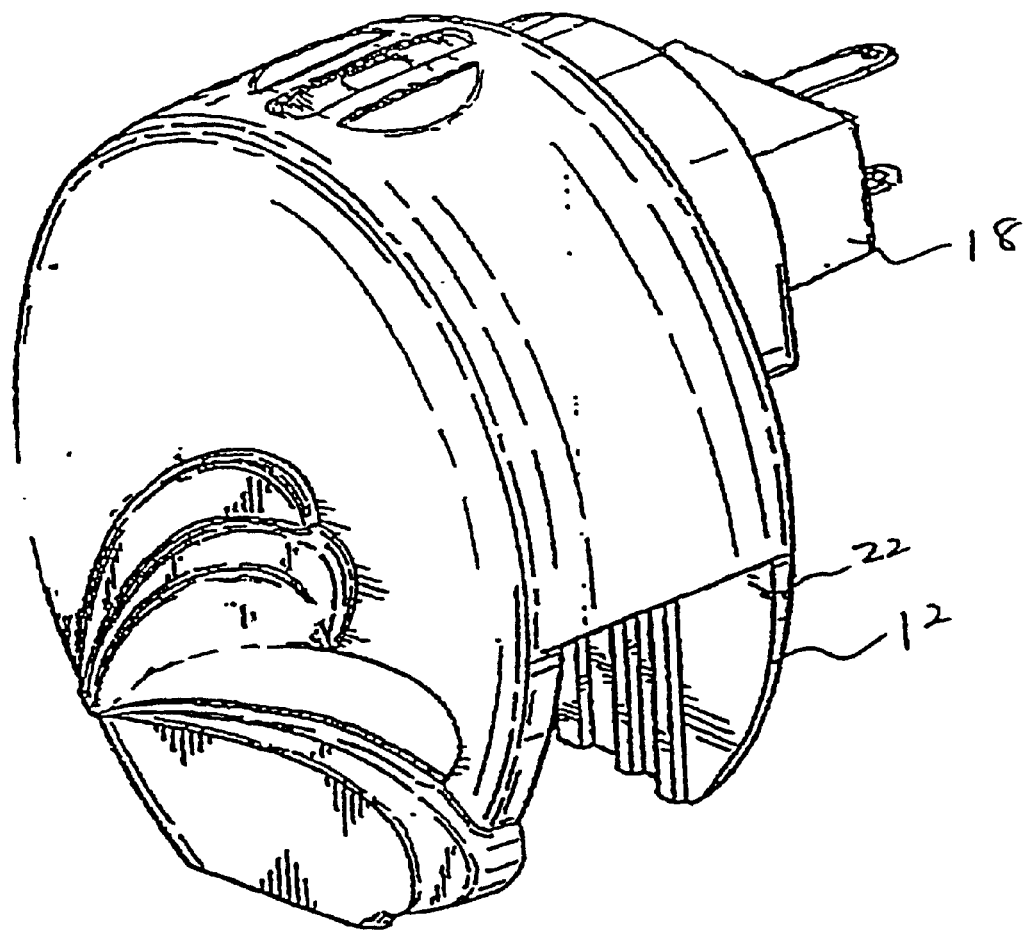
FIG. 15 is a perspective view of a housing unit for use in connection with the bottle unit shown in FIG. 9.

With reference now to FIGS. 12–14, it should be appreciated that the particular configuration of groove 72 may be modified as may be deemed appropriate for any application. That is, in the event a single projection is provided on housing unit 12 (or in certain instances on refill bottle 14 corresponding to an appropriately shaped groove on refill housing 12) the shape and size of that groove may be modified. For example, FIG. 12 illustrates a typical projection 72 such as may be used in connection with forming system 10 of FIG. 1. It should be appreciated, however, that the width of groove 72 may be modified, i.e., narrowed, such as is shown in FIG. 13 as projection 72A, or the width may be varied over the length of projection 72, such as shown as projection 72B in FIG. 14. These and other modifications as are now known or hereafter devised by those skilled in the art may be made in light of the foregoing teachings.

It should be appreciated that the guidance system thus described also can aid in ease of and safety of removal of bottle unit 14 from housing unit 12. For example, if it is desired to replace bottle unit 14 with another bottle unit, perhaps to change the fragrance with emanated through use of system 10, it is desirable to enable removal of bottle unit 14 while protecting wick 40 from damage and/or contact with the warmer unit contained within system 10. The foregoing guidance systems enable such removal.

As previously mentioned, the present inventors have found that in addition to the guidance system which provides benefits with respect to ease of insertion and removal, a stabilization system may be provided which enhances stabilization of bottle unit 14 with respect to housing unit 12.

In general, bottle stabilization is accomplished through provision of opposing securement mechanisms. For example, in the context of the embodiment just described and with reference to FIGS. 1 and 6, bottle 14 is stabilized within housing 14 by the interconnection of element 32 within aperture 34 together with the provision of projection 70 which fits within groove 72. As shown, in general, the opposing securement mechanisms are oriented along different axes of bottle 14, or the system 10. In this case, projection 70 and groove 72 are generally oriented along the Y axis of system 10, whereas element 32 and aperture 34 are generally oriented along the X axis of system 10. Preferably, the orientation of the opposing securement mechanisms will be substantially perpendicular. However, other non-perpendicular arrangements may be utilized for this purpose. It should be appreciated that other configurations, as well as other securement mechanisms may be utilized to stabilize bottle 14 within housing unit 12.

Figure 17:
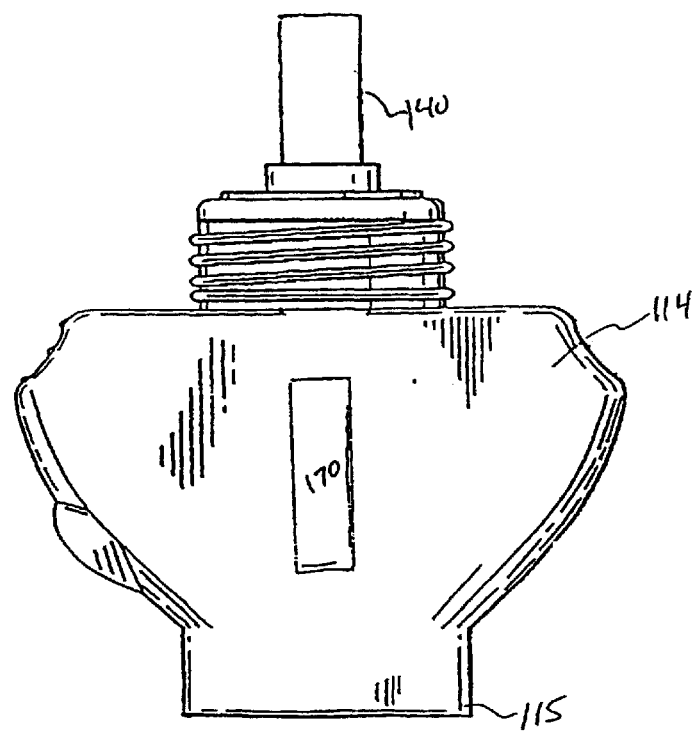
FIG. 17 is a back view of a further embodiment of a bottle unit useful in accordance with the present invention.
Figure 16:
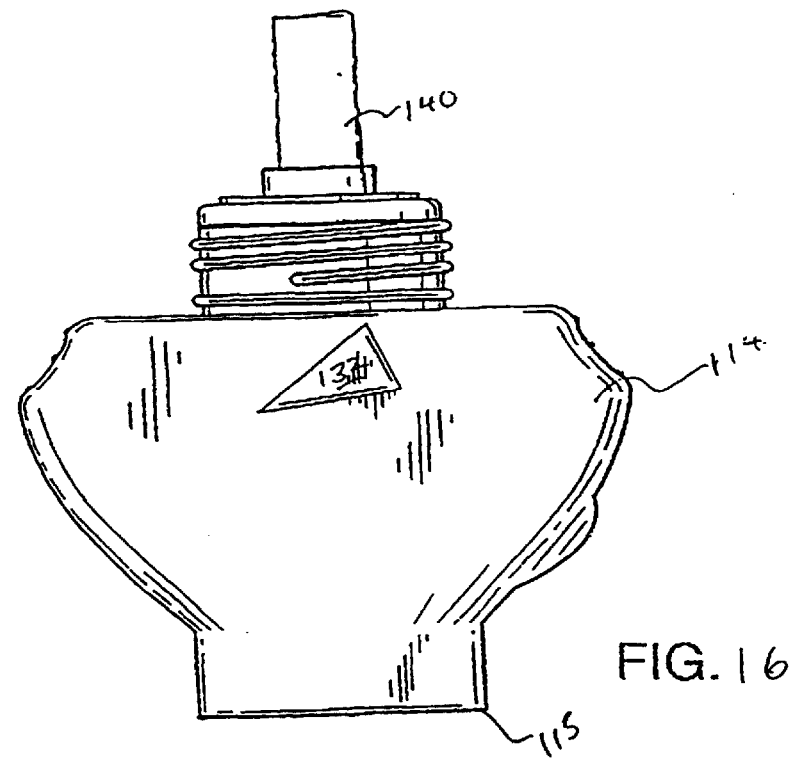
FIG. 16 is a front view of an alternative embodiment of a bottle unit useful in accordance with the present invention.
Figure 18:
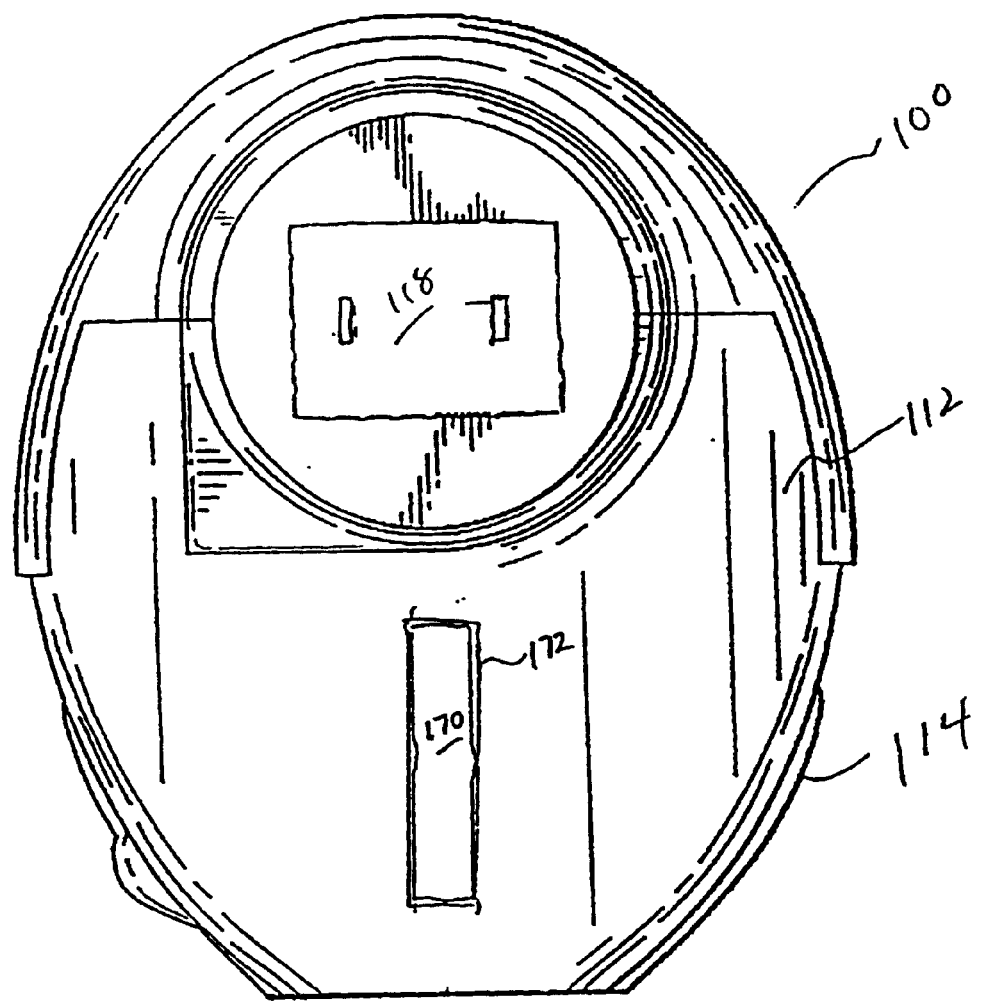
FIG. 18 is a back view of a liquid vaporizer incorporating the bottle unit shown in FIG. 17.

For example, and with reference now to FIGS. 16–18, a further embodiment of the present invention is shown in connection with a system 100. As shown in FIG. 18, system 100 preferably includes a refill bottle unit 114 which is suitably configured for receipt within a housing 112. As with system 10, system 100 preferably includes a plug unit, namely the plug unit 118, and in general operates in a manner similar to that described with respect to system 10 hereinabove. As shown in FIG. 17, bottle 114 may be configured to include an elongate section 115 extending from the bottom surface thereof. Bottle 114 is suitably configured for receipt of a wick 140. The front surface of bottle 114 is suitably provided with a projection 132 which is configured for receipt within an aperture (not shown) configured in the same fashion as aperture 34 of system 10. In lieu of use of the guiding system shown in connection with system 10, system 100 employs an elongate projection 170 provided on the rear surface of bottle 114. Projection 170 is suitably configured for receipt within a substantially corresponding aperture 172 provided in the back surface of housing 112. The opposing securement mechanisms, namely securement through use of projection 132 and projection 170, which projections are generally opposed in orientation, serves to stabilize bottle 114 within housing unit 112.

From the foregoing discussion it should be appreciated that various other configurations may be utilized. For example, and in accordance with a preferred embodiment of the present invention, the aforementioned guidance system serves as one securement mechanism and is generally oppositely disposed with respect to the "snap-and-fit" arrangement, i.e., interconnection between element 32 and aperture 34, such that bottle stabilization is enhanced. However, multiple projections, grooves and corresponding indentations and/or other combinations of elements may be utilized.

Figure 4A:
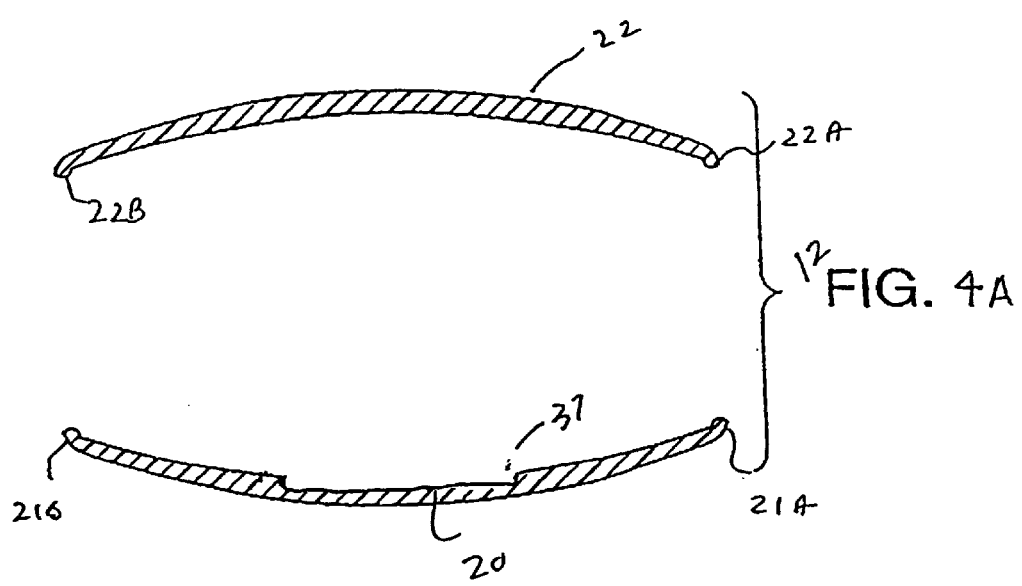
FIG. 4A is a sectional view taken along the line A—A of FIG. 4.

Stabilization of the bottle unit with respect to the housing unit may be further enhanced through the configuration of the housing unit relative to the bottle unit. With reference now to FIGS. 4, 4A, and 5, in accordance with various preferred aspects of the present invention, housing 12 is suitably configured to substantially conform to the shape and configuration of refill bottle unit 14. In this regard, the bottom opening 26 within housing unit 12 preferably has an inside dimension X at the outermost point of between about 35 and about 40 millimeters. Preferably, dimension X is between about 35 and about 37 millimeters. Preferably, opening 26 has an uppermost dimension X' of between about 15 and about 20 millimeters, more preferably on the order of about 15 millimeters. Such a configuration enables a bottle 14, as previously described, to be suitably force-fitted within opening 26 of housing 12.

With reference now to FIGS. 4A and 5, preferably walls 20 and 22 of housing 12 are suitably configured to "wrap" around refill bottle 14. For example, as shown in FIGS. 4A and 5, each of walls 20 and 22 are suitably provided with respective corners 21A, 21B and 22A, 22B which evidence a radius of curvature such that the outermost ends of each of walls 20 and 22 are suitably inwardly directed to retain bottle 14 within opening 26.

It should be appreciated that various other stabilization systems and/or mechanisms may be utilized in accordance with the present invention.

In accordance with preferred aspects of the present invention, the stabilization and guidance system just described are preferably used in connection with the "snap-and-fit" connection between refill bottle 14 and housing unit 12 (for example, projection 32 contained on front surface 50 of refill bottle unit 14 and aperture 34 formed on front surface 20 of housing unit 12). However, other or additional attachment mechanisms may be utilized to secure refill bottle 14 to housing unit 12. For example, attaching devices comprising bayonet attachments, undercuts with matching projections and the like may be utilized. In addition, hooks may be provided on the bottom of bottle 14.

Alternatively, side wall 54 of refill bottle unit 14 may be configured in the uppermost portion with attachment devices for enabling attachment to the inner portion of housing unit 12. As shown, for example in FIG. 11, preferably side wall 54 is provided in proximity to top 56 with a plurality of knurls 86 which aid in enabling the user to insert and remove refill bottle unit 14 from housing unit 12. In certain applications, it may be desirable to further configure a lock and latch attachment mechanism in connection with knurls 86 such that by squeezing the bottle, one might disengage refill bottle unit 14 from housing unit 12.

Moreover, various attachment mechanisms may be utilized in connection with neck 58. For example, housing unit may be configured in the form of a socket which is engageable with one or more of the thread portions of other projections placed on or about neck 58 of refill bottle unit 14. In either case, the guidance system in accordance with the present invention may be utilized to enhance performance and ease of application of a liquid vaporizer so configured.

In accordance with yet another aspect of the present invention, a housing stabilization system is provided which acts to promote stabilization of housing unit 12 when it is inserted into a socket of a conventional wall outlet. With reference to FIGS. 19 through 22, a preferred embodiment of housing stabilization system 200 is shown. Preferably, housing stabilization system 200 is configured to extend from back surface 22 of vaporizer 10. In accordance with various aspects of the present invention, stabilization system 200 is physically integrated with housing 12, as well as formed from the same material as housing 12. For example, as mentioned previously, preferably like housing 12, housing stabilization system comprises a plastic material such as polypropylene or high-density polyethylene. However, in accordance with various applications, it may be desirable for stabilization system to be formed of other substantially rigid materials.

In the present exemplary embodiment stabilization system 200 is located proximate to an upper area 202 of backing 22 and comprises a substantially U-shaped structure. Of course it should be appreciated system 200 may be located in other areas of vaporizer 10, for example, in positions more proximate to the center of back 22 or towards the lower portion of housing 12.

Preferably, stabilization system 200 extends substantially the same length as a plug backing 19 of plug structure 18. Thus, when vaporizer 10 is inserted into a conventional wall outlet, plug backing 19 substantially abuts the outlet itself and/or the wall against which the outlet is incorporated, while a back surface 204 of stabilization system 200 likewise abuts the outlet or the wall to which the vaporizer 10 is inserted. Such abutment suitably minimizes movement of vaporizer 10 when inserted in the wall. Such movement may include rotation in the vertical or horizontal direction, or simply movement attendant to the weight of vaporizer 10 and/or inadvertent blows to vaporizer 10. In general, housing stabilization system 200 is configured and positioned to minimize such movements; stated another way, the stabilization provided by stabilization system 200 tends to inhibit or at least reduce such movement.

Figure 23:
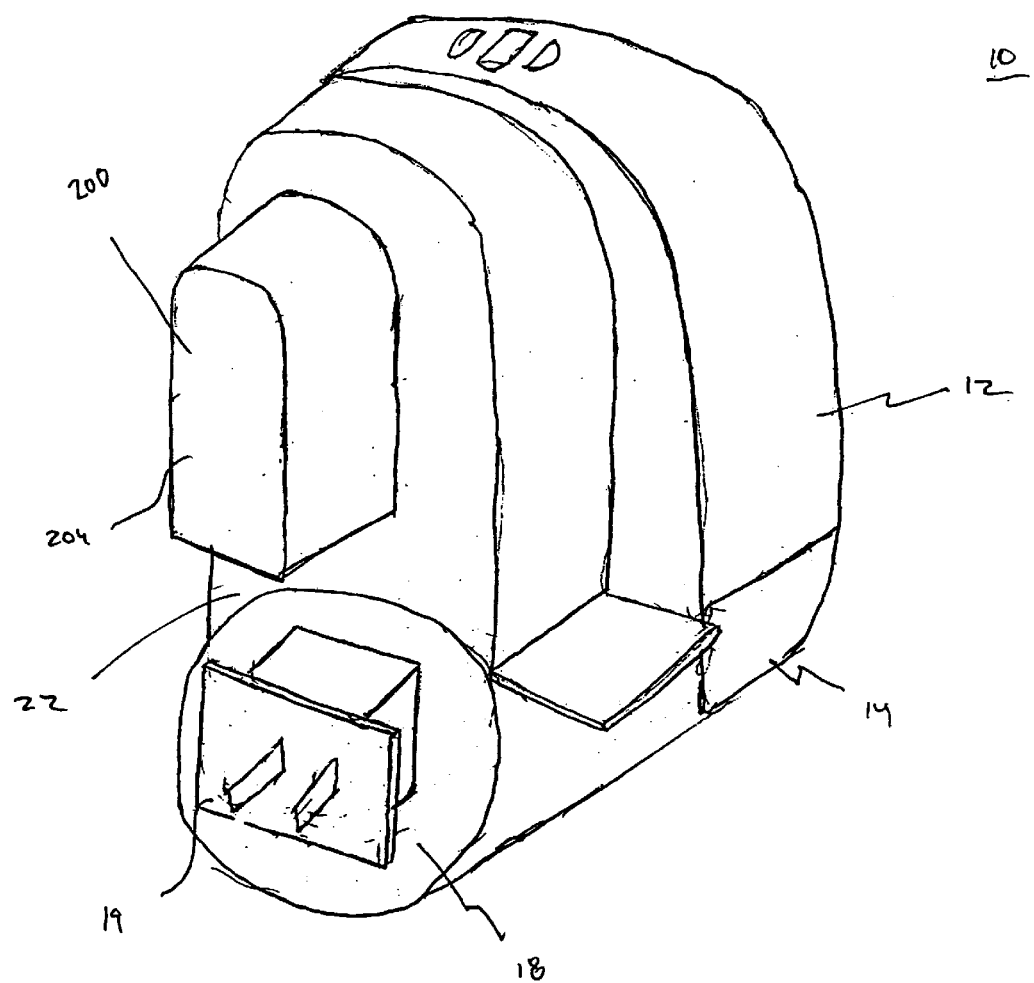
FIG. 23 is a rear perspective view of an alternative embodiment of an electric liquid vaporizer in accordance with the present invention.

Various alternative embodiments of stabilization system 200 may also be configured on vaporizer 10. For example, with reference now to FIG. 23, stabilization system 200, while remaining substantially U-shaped, the "U section" may be filled in or substantially covered over, for example, to increase back surface 204. Similarly, while the present exemplary embodiments are directed largely to U or circular shaped stabilization systems, it should likewise be apparent that any shape which provides additional points of contact away from plug structure 18 and/or which substantially abut the wall or outlet when vaporizer 10 is inserted into the outlet may likewise be employed. For example, stabilization system 200 may be comprised as square, triangular, oval or otherwise. Further still, stabilization system 200 may be configured with multiple projections.

Figure 24:
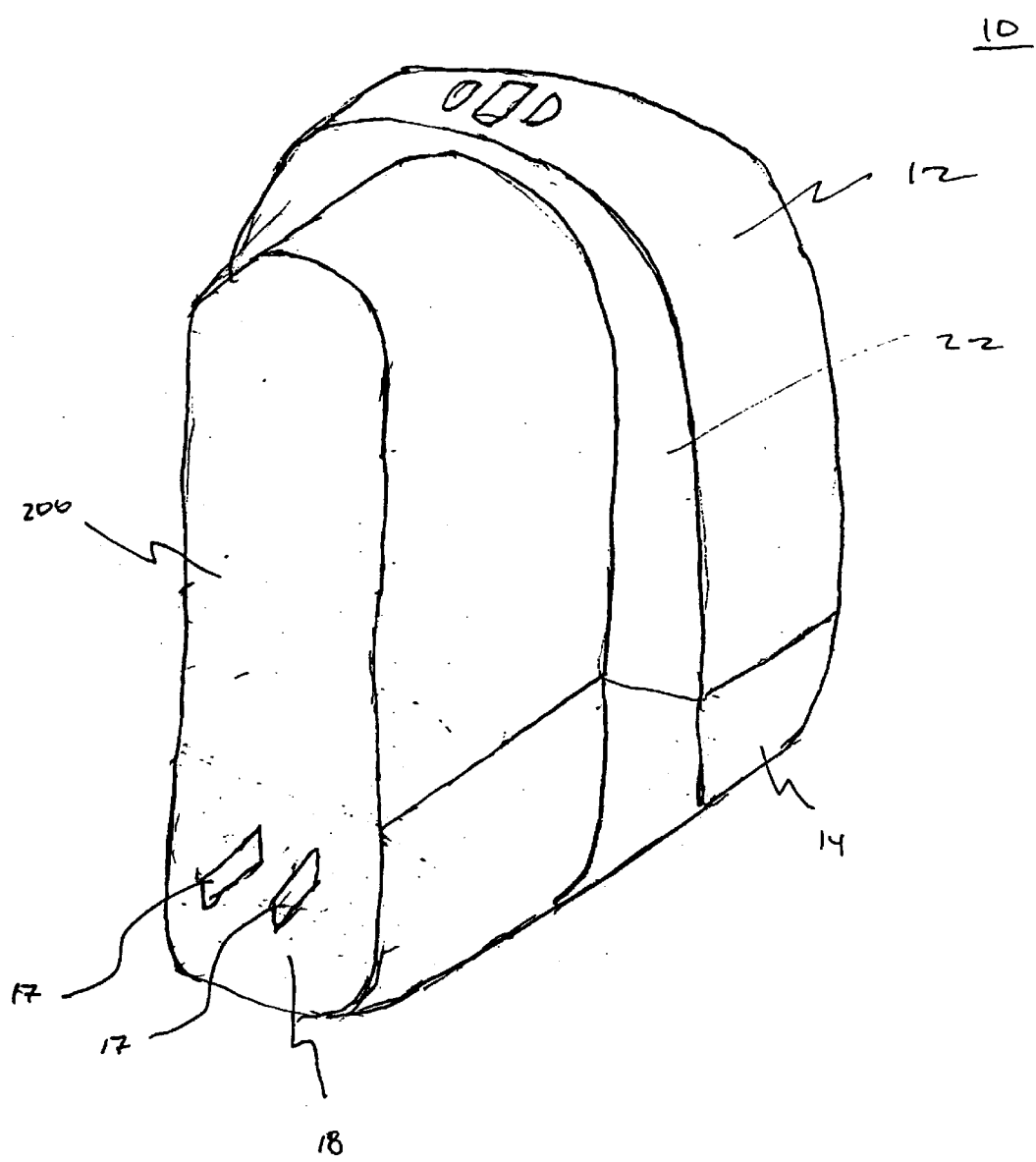
FIG. 24 is a rear perspective view of a further embodiment of an electric liquid vaporizer in accordance with the present invention.
Figure 25:
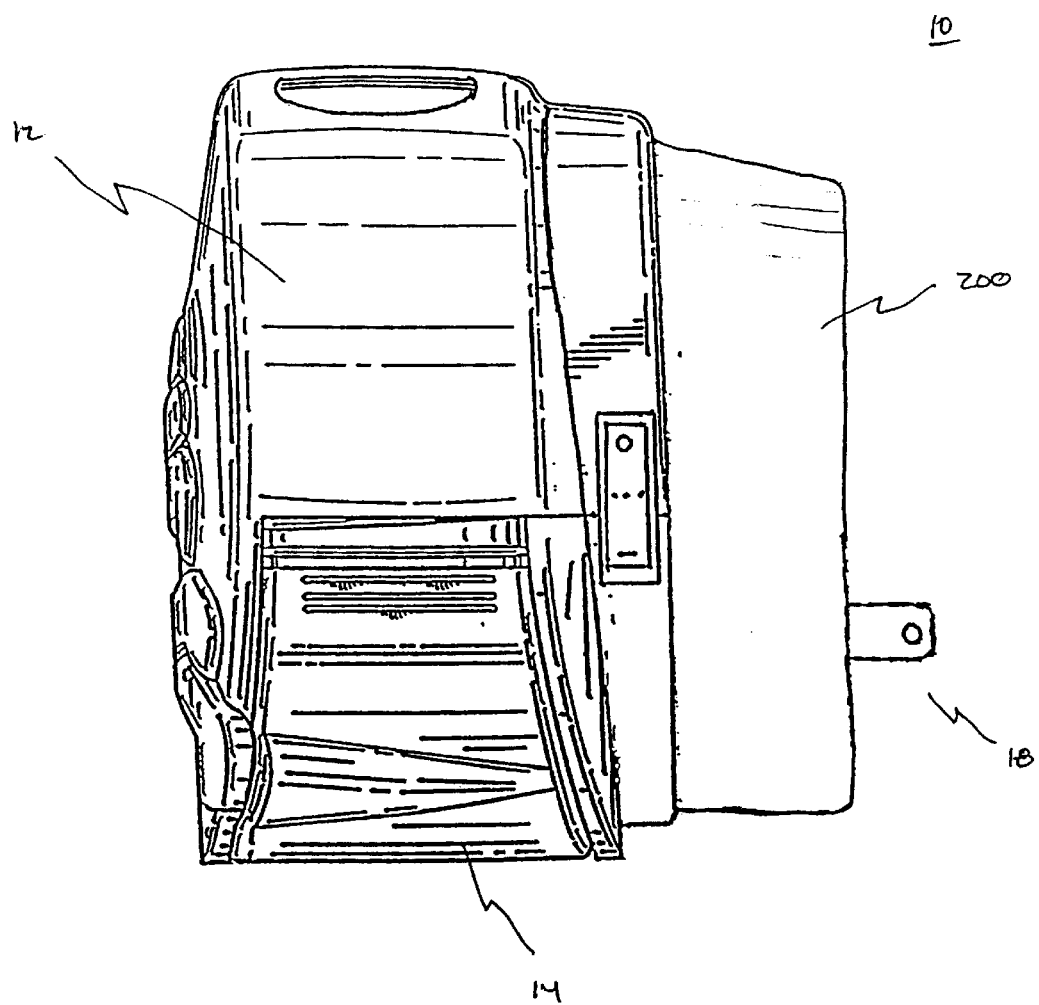
FIG. 25 is a side view of the liquid vaporizer of FIG. 24.
Figure 26:
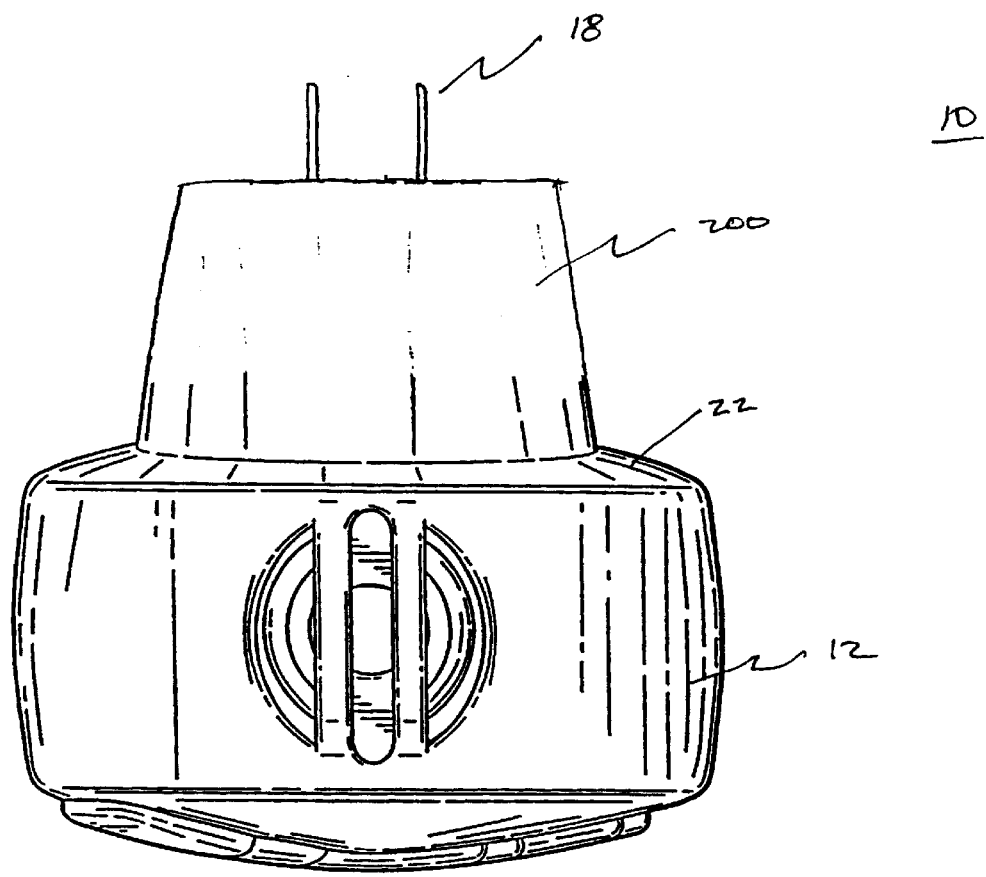
FIG. 26 is a top plan view of the housing unit of FIG. 24.

In accordance with still another aspect of the present invention, stabilization system 200 may suitably comprise a structure which is integrated with plug structure 18 such that the surface contact of plug structure 18 and/or stabilization system 200 and/or the distance between contact between the wall and vaporizer 10 is increased, thereby increasing surface contact and/or the distance between contact between the wall and vaporizer 10. In accordance with this aspect of the invention and now with reference to FIG. 24, stabilization system 200 may comprise an integrated projection extending from housing back 22. Integrated projection 200 comprises any structure which suitably provides increased surface area and/or contact between vaporizer 10 and the outlet to which vaporizer 10 is inserted or the surrounding structure (e.g., the wall). For example, as shown in FIG. 24, integrated structure 200 may comprise an oval shaped projection which encompasses plug 18, leaving only the electrical prongs 17 of plug 18 extending from integrated structure 200. Thus, when vaporizer 10 is inserted into a wall outlet, integrated structure 202 substantially abuts the wall or outlet along substantially its entire back surface 204. Accordingly, increased stabilization is provided.

In accordance with yet another aspect of the present invention, plug 18 is located on vaporizer 10 such that venting 16 is provided in a safe and effective manner. For example with reference to FIGS. 19 through 26, in accordance with various aspects of this embodiment of the present invention, plug 18 provided at an increased distance from the wall outlet for example, located proximate to an end opposite vents 16. As shown best in FIG. 19, vents 16 can be located on a top side of vaporizer 10, and plug 18 located proximate to the opposite end, the lower portion, of vaporizer 10. Thus, when vaporizer 10 is inserted into a wall outlet, vents 16 are generally an increased distance from the wall and/or outlet. It should be appreciated that plug 18 may be located at any distance from vents 16, and depending on length of vaporizer 10, is located at any distance proximate a middle portion of vaporizer 10 to end.

In accordance with yet another aspect of the present invention, stabilization system 200 may also serve to further maintain vents 16 some distance from the electrical socket to which vaporizer 10 is inserted. Additionally, stabilization system 200 may also serve to maintain vents 16 from other electrical sockets proximate to that which vaporizer 10 is inserted. For example, as noted above, in accordance with one aspect of the present invention, stabilization system 200 is about the same length as plug structure 18. Thus, when vaporizer 10 is inserted into the wall outlet, stabilization system 200 maintains the upper portion of vaporizer 10, the portion near vents 16, away from the wall, and thus away from the outlet as well.

Figure 32:
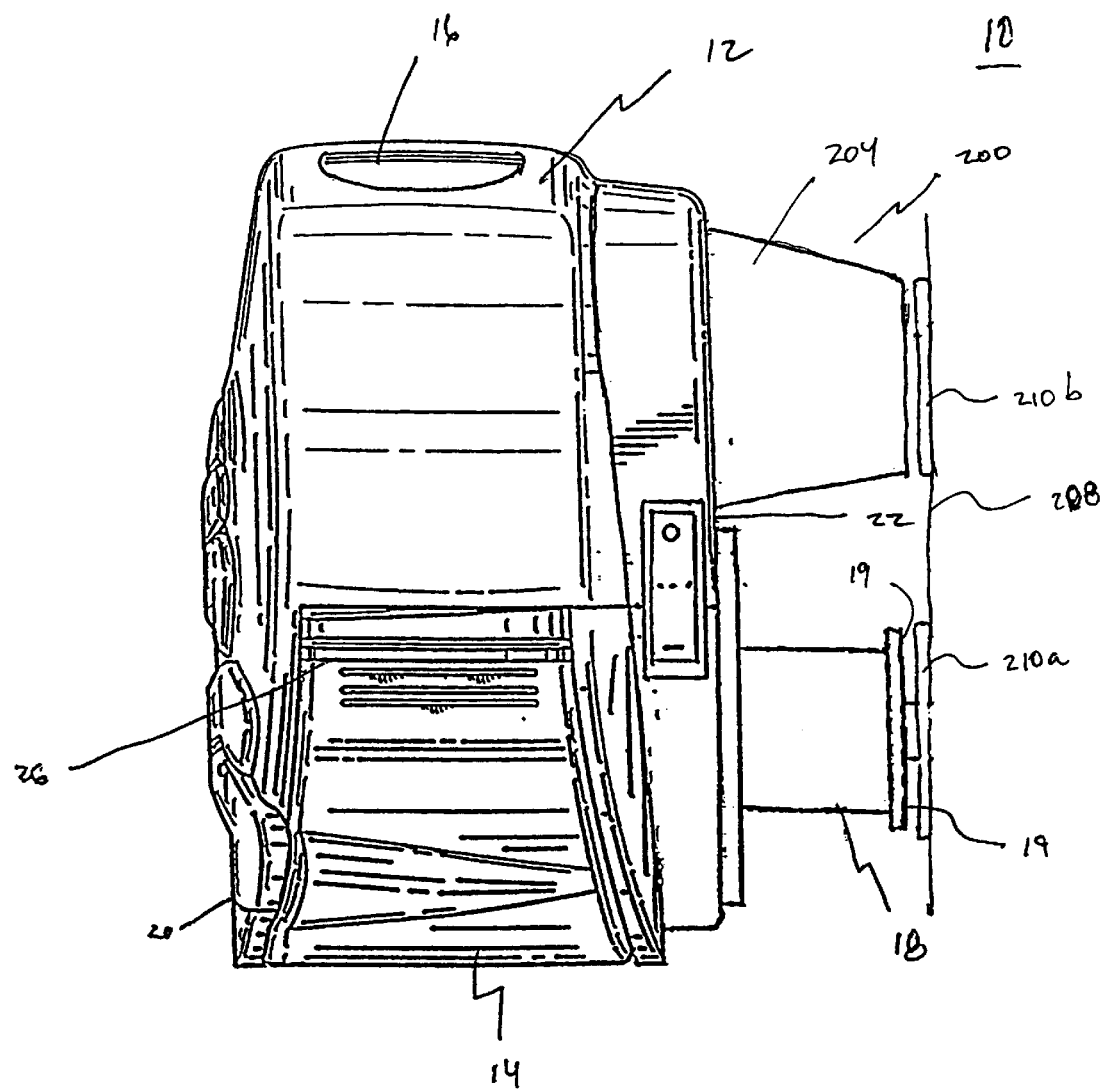
FIG. 32 is a front view of a plug and wiring system in accordance with another embodiment of the present invention

According to yet another alternative aspect the present invention, stabilization system 200 also serves to provide a barrier which prevents vaporized material from entering the electrical socket. For example, in the exemplary embodiment of FIG. 32, when vaporizer 10 is plugged into a conventional two socket wall outlet 208, wherein two sockets 210a,b are vertically oriented, and vaporizer 10 is plugged into lower wall outlet 210a, stabilization system 200 suitably provides a barrier covering upper wall outlet 210b. Thus, any vaporized material is suitably isolated from the electrical sockets of the wall outlet.

The present invention has been described above with reference to various preferred embodiments. However, those skilled in the art will recognize that changes and modifications may be made to various preferred embodiments without departing from the scope of the present invention. For example, various additions to aid in attachment of refill bottle unit 14 to housing unit 12 may be provided. Further, various changes in the configuration of the housing unit, plug unit and/or heating unit may be made without departing from the scope of the present invention. Moreover, guidance and stabilization systems may be augmented or modified in accordance with the various teachings herein provided. These and other changes or modifications are intended to be included within the scope of the present invention as set forth in the appended claims.

We claim:

1. An improved vapor dispensing device of the type comprising a refill bottle including a wick in fluid communication with a material to be dispensed contained within said refill bottle and extending into proximity with a heater unit contained within a housing unit, the improvement comprising, said housing unit defining a back surface area and having an electric plug structure body from which plug prongs extend and a stabilizing portion, each of said stabilizing portion and said electric plug structure body extending from said back surface area, wherein said stabilizing portion is distinct and spatially displaced from said electric plug structure body, to minimize rotation of the dispensing device about said plug structure when the dispensing device is placed in an outlet.

2. The vapor dispensing device of claim 1, wherein said stabilizing portion projects from said back surface about the same distance from said housing back as said electric plug structure body.

3. The vapor dispensing device of claim 2, wherein said electric plug structure body is proximate to a lower area of said back surface and said stabilizing projection is proximate to an upper area of said back surface.

4. The vapor dispensing device of claim 2, wherein said stabilizing portion minimizes dispensement of said material to be dispensed in the vicinity of said outlet.

5. The vapor dispensing device of claim 2, wherein said stabilizing portion minimizes dispensement of said material to be dispensed in the vicinity of said outlet by maintaining said housing away from said outlet.

6. The vapor dispensing device of claim 1, wherein said stabilizing portion provides a baffier between vaporized material and said outlet.

7. The vapor dispensing device of claim 1, wherein when the dispensing device is inserted into a lower outlet, said stabilizing portion substantially covers an upper outlet.

8. The vapor dispensing device of claim 1, wherein said stabilizing portion is about the same length as a base of said electric plug structure body of the vapor dispensing device.

* * * * *